US011672761B2

(12) United States Patent
Mileto et al.

(10) Patent No.: US 11,672,761 B2
(45) Date of Patent: Jun. 13, 2023

(54) RAPIDLY INFUSING PLATFORM AND COMPOSITIONS FOR THERAPEUTIC TREATMENT IN HUMANS

(71) Applicant: Orcosa Inc., Ewing, NJ (US)

(72) Inventors: Vincent T Mileto, Flemington, NJ (US); Simon Winslow, Bethlehem, PA (US); Mark Ridall, Skillman, NJ (US)

(73) Assignee: Orcosa Inc., Ewing, NJ (US)

( * ) Notice: Subject to any disclaimer, the term of this patent is extended or adjusted under 35 U.S.C. 154(b) by 0 days.

(21) Appl. No.: 17/225,738

(22) Filed: Apr. 8, 2021

(65) Prior Publication Data

US 2022/0151934 A1    May 19, 2022

Related U.S. Application Data

(60) Provisional application No. 63/114,194, filed on Nov. 16, 2020.

(51) Int. Cl.
| | |
|---|---|
| *A61K 9/19* | (2006.01) |
| *A61K 31/05* | (2006.01) |
| *A61K 9/00* | (2006.01) |
| *A61P 23/00* | (2006.01) |
| *A61K 9/14* | (2006.01) |
| *A61K 31/4045* | (2006.01) |

(52) U.S. Cl.
CPC .............. *A61K 9/19* (2013.01); *A61K 9/0053* (2013.01); *A61K 9/145* (2013.01); *A61K 9/146* (2013.01); *A61K 31/05* (2013.01); *A61K 31/4045* (2013.01); *A61P 23/00* (2018.01)

(58) Field of Classification Search
CPC ........ A61K 9/19; A61K 9/0053; A61K 9/145; A61K 9/146; A61K 9/006; A61K 9/2063; A61K 31/05; A61K 31/4045; A61P 23/00
See application file for complete search history.

(56) References Cited

U.S. PATENT DOCUMENTS

| | | | |
|---|---|---|---|
| 3,894,896 A | 7/1975 | Watanabe | |
| 5,112,616 A * | 5/1992 | McCarty | A61K 9/0056 424/464 |
| 5,343,672 A | 9/1994 | Kearney et al. | |
| 5,631,023 A | 5/1997 | Kearney et al. | |
| 5,720,974 A | 2/1998 | Makino et al. | |
| 5,729,958 A | 3/1998 | Kearney et al. | |
| 6,007,824 A | 12/1999 | Duckett et al. | |
| 6,307,346 B1 | 10/2001 | Downer et al. | |
| 6,316,027 B1 | 11/2001 | Johnson et al. | |
| 6,316,029 B1 | 11/2001 | Jain et al. | |
| 6,391,237 B1 | 5/2002 | Kearney et al. | |
| 6,509,040 B1 | 1/2003 | Murray et al. | |
| 6,534,094 B2 | 3/2003 | Moyano et al. | |
| 6,709,669 B1 * | 3/2004 | Murray | A61K 9/2063 424/434 |
| 6,830,153 B2 | 12/2004 | French et al. | |
| 6,860,405 B1 | 3/2005 | Poynter | |
| 7,090,866 B2 | 8/2006 | Johnson et al. | |
| 7,135,180 B2 | 11/2006 | Truong-Le | |
| 7,331,460 B2 | 2/2008 | Barndt et al. | |
| 7,360,652 B2 | 4/2008 | Arnold | |
| 7,393,674 B2 | 7/2008 | Jiang et al. | |
| 7,464,818 B2 | 12/2008 | Gherdan et al. | |
| 7,607,834 B2 | 10/2009 | Alvater et al. | |
| 7,771,745 B2 | 8/2010 | Wang et al. | |
| 7,799,860 B2 | 9/2010 | Sugishita et al. | |
| 7,951,397 B2 | 5/2011 | Dietrich et al. | |
| 7,968,594 B2 | 6/2011 | Guy et al. | |
| 7,972,621 B2 | 7/2011 | Wong et al. | |
| 8,268,354 B2 | 9/2012 | Truong-Le et al. | |
| 8,445,524 B2 | 5/2013 | Courvoisier et al. | |
| 8,545,836 B2 | 10/2013 | Kaul et al. | |
| 8,545,879 B2 | 10/2013 | Burns et al. | |
| 8,598,207 B2 | 12/2013 | Buehler | |
| 8,647,668 B2 | 2/2014 | Tanaka et al. | |
| 8,722,366 B2 | 5/2014 | Sasaki et al. | |

(Continued)

FOREIGN PATENT DOCUMENTS

| | | |
|---|---|---|
| AU | 2019379706 A1 | 6/2021 |
| CN | 1320887 C | 6/2007 |

(Continued)

OTHER PUBLICATIONS

Zhu et al., An evaluation of anti-hyperalgesic effects of cannabidiolic acid-methyl ester in a preclinical model of peripheral neuropathic pain, Jun. 2020, British Journal of Pharmacology, vol. 177 iss. 12, pp. 2712-2725. (Year: 2020).*

Ward et al., Cannabidiol inhibitspaclitaxel-inducedneuropathic pain through5-HT1Areceptors withoutdiminishing nervous systemfunction or chemotherapyefficacy, Oct. 4, 2013, British Journal of Pharmacology, vol. 171, pp. 636-645. (Year: 2013).*

"Tablet," Stedman's Medical Dictionary (1972), 22nd ed, p. 1250.

"Tablet," Stedman's Medical Dictionary (1990), 25th ed, pp. 1549-1550.

(Continued)

*Primary Examiner* — Ali Soroush

(74) *Attorney, Agent, or Firm* — Oblon, McClelland, Maier & Neustadt, L.L.P.

(57) ABSTRACT

A composition and method of treatment in a subject, whereby the subject is administered via the oral mucosa a rapidly infusing composition that includes (a) a pharmaceutically acceptable binder and/or excipient system containing gelatin and mannitol, and (b) a therapeutically effective amount of an active therapeutic ingredient (ATI). Preferably, a composition and method of treating pain in a subject, whereby the subject is administered via the oral mucosa a rapidly infusing composition that includes (a) a pharmaceutically acceptable binder and/or excipient system containing gelatin and mannitol, and (b) a therapeutically effective amount cannabidiol (CBD).

33 Claims, 1 Drawing Sheet

(56) References Cited

U.S. PATENT DOCUMENTS

| | | | |
|---|---|---|---|
| 8,802,145 B2 | 8/2014 | Bauer | |
| 8,865,722 B2 | 10/2014 | Hrakovsky et al. | |
| 8,946,153 B2 | 2/2015 | Gupta et al. | |
| 8,974,824 B2 | 3/2015 | Amminabavi et al. | |
| 9,066,870 B2 | 6/2015 | Hu et al. | |
| 9,119,794 B2 | 9/2015 | Middlbeek et al. | |
| 9,241,902 B2 | 1/2016 | Rowe et al. | |
| 9,265,764 B2 | 2/2016 | Haggarty et al. | |
| 9,408,879 B2 | 8/2016 | Guglielmetti et al. | |
| 9,415,015 B2 | 8/2016 | Jacobi et al. | |
| 9,468,679 B2 | 10/2016 | Debunne et al. | |
| 9,492,379 B2 | 11/2016 | Park et al. | |
| 9,629,920 B2 | 4/2017 | Leighton et al. | |
| 9,717,681 B2 | 8/2017 | Banbury et al. | |
| 9,717,684 B2 | 8/2017 | Bhavsar et al. | |
| 9,717,692 B2 | 8/2017 | Bilgic | |
| 9,731,018 B2 | 8/2017 | Ahuja et al. | |
| 9,775,819 B2 | 10/2017 | Bahl et al. | |
| 9,808,521 B2 | 11/2017 | Weigandt et al. | |
| 9,820,937 B2 | 11/2017 | Brewer et al. | |
| 9,833,408 B1 | 12/2017 | Greenspoon | |
| 9,839,613 B2 | 12/2017 | Qiao et al. | |
| 9,872,873 B2 | 1/2018 | Khattar et al. | |
| 9,895,342 B2 | 2/2018 | Maione et al. | |
| 9,901,603 B2 | 2/2018 | Borody | |
| 9,956,169 B2 | 5/2018 | Tian et al. | |
| 9,974,826 B2 | 5/2018 | Klein et al. | |
| 9,980,915 B2 | 5/2018 | Matsuoka et al. | |
| 10,064,849 B2 | 9/2018 | Ridall et al. | |
| 10,086,078 B2 | 10/2018 | Ahuja et al. | |
| 10,137,167 B2 | 11/2018 | Klein et al. | |
| 10,226,525 B2 | 3/2019 | Anderson et al. | |
| 10,307,394 B2 | 6/2019 | Chistov | |
| 10,307,397 B2 | 6/2019 | Allen et al. | |
| 10,307,459 B2 | 6/2019 | Nilsson et al. | |
| 10,383,911 B2 | 8/2019 | Abels et al. | |
| 10,420,809 B2 | 9/2019 | Crowley | |
| 10,548,839 B2 | 2/2020 | Tian | |
| 10,604,467 B2 | 3/2020 | Emanuele et al. | |
| 10,617,650 B2 | 4/2020 | Bhambhani et al. | |
| 10,624,940 B2 | 4/2020 | Speier | |
| 10,632,164 B2 | 4/2020 | Schaneville | |
| 10,695,332 B2 | 6/2020 | Ridall et al. | |
| 10,799,467 B2 | 10/2020 | Whalley et al. | |
| 10,888,518 B2 | 1/2021 | Jaspart et al. | |
| 10,888,519 B2 | 1/2021 | Soni et al. | |
| 10,905,681 B2 | 2/2021 | Wrobel et al. | |
| 10,925,853 B2 | 2/2021 | Bruun et al. | |
| 10,928,829 B2 | 2/2021 | Tatourian et al. | |
| 10,973,766 B2 | 4/2021 | Pillay et al. | |
| 10,988,638 B2 | 4/2021 | Wong et al. | |
| 11,000,480 B2 | 5/2021 | Deshpande et al. | |
| 2003/0017209 A1 | 1/2003 | Parikh et al. | |
| 2003/0229027 A1 | 12/2003 | Eissens et al. | |
| 2004/0023948 A1 | 2/2004 | Green et al. | |
| 2004/0076666 A1 | 4/2004 | Green et al. | |
| 2004/0156894 A1* | 8/2004 | Grother | A61K 9/0056 424/465 |
| 2005/0042177 A1 | 2/2005 | Ryde et al. | |
| 2006/0093679 A1 | 5/2006 | Mayer et al. | |
| 2006/0134195 A1 | 6/2006 | Fu et al. | |
| 2007/0122355 A1 | 5/2007 | Monteith et al. | |
| 2007/0134493 A1 | 6/2007 | Meghpara | |
| 2007/0259857 A1 | 11/2007 | Gray | |
| 2007/0298090 A1 | 12/2007 | Chen et al. | |
| 2008/0200452 A1 | 8/2008 | Obermeier et al. | |
| 2008/0213343 A1 | 9/2008 | Obermeier et al. | |
| 2008/0251411 A1 | 10/2008 | Walker et al. | |
| 2008/0305168 A1 | 12/2008 | Moon et al. | |
| 2009/0226522 A1 | 9/2009 | Howes et al. | |
| 2010/0239646 A1 | 9/2010 | Nair | |
| 2011/0097395 A1* | 4/2011 | Babul | A61K 9/1652 424/451 |
| 2011/0217313 A1 | 9/2011 | Becker et al. | |
| 2011/0268809 A1 | 11/2011 | Brinkley et al. | |
| 2012/0165413 A1 | 6/2012 | Fujiwara et al. | |
| 2013/0039981 A1 | 2/2013 | Cherurkuri | |
| 2014/0079756 A1 | 3/2014 | Andersen et al. | |
| 2015/0133504 A1 | 5/2015 | Ridall et al. | |
| 2016/0015683 A1 | 1/2016 | McCarty | |
| 2016/0058866 A1 | 3/2016 | Sekura et al. | |
| 2016/0159541 A1 | 6/2016 | Brandl | |
| 2016/0243055 A1* | 8/2016 | Yeshurun | A61K 45/06 |
| 2017/0112762 A1 | 4/2017 | Sivert et al. | |
| 2017/0295817 A1 | 10/2017 | Rojano Jorge et al. | |
| 2017/0319433 A1 | 11/2017 | Hosoi et al. | |
| 2017/0326147 A1 | 11/2017 | Sa et al. | |
| 2017/0348249 A1 | 12/2017 | Sune Negre et al. | |
| 2018/0064645 A1 | 3/2018 | Greenspoon | |
| 2018/0092853 A1 | 4/2018 | Hassan et al. | |
| 2018/0110810 A1 | 4/2018 | Sadowsky et al. | |
| 2018/0153794 A1 | 6/2018 | Coric et al. | |
| 2018/0169022 A1 | 6/2018 | Jaspart et al. | |
| 2018/0279641 A1 | 10/2018 | Dong | |
| 2018/0311205 A1 | 11/2018 | Morgan | |
| 2018/0369221 A1 | 12/2018 | Ridall et al. | |
| 2019/0008848 A1 | 1/2019 | Zhang et al. | |
| 2019/0008870 A1 | 1/2019 | Chen | |
| 2019/0070124 A1* | 3/2019 | Anavi-Goffer | A61K 31/015 |
| 2019/0083391 A1 | 3/2019 | Bond | |
| 2019/0083611 A1 | 3/2019 | Yi | |
| 2019/0307675 A1 | 10/2019 | Rosenbaum et al. | |
| 2019/0314274 A1 | 10/2019 | Masto et al. | |
| 2019/0314368 A1 | 10/2019 | Liang et al. | |
| 2019/0328673 A1 | 10/2019 | Wan et al. | |
| 2019/0388392 A1 | 12/2019 | Ahmed et al. | |
| 2020/0009232 A1 | 1/2020 | Fuhrherr et al. | |
| 2020/0022945 A1 | 1/2020 | Swartout | |
| 2020/0022993 A1 | 1/2020 | Zhong et al. | |
| 2020/0054563 A1 | 2/2020 | Li et al. | |
| 2020/0061138 A1 | 2/2020 | Williams | |
| 2020/0115317 A1 | 4/2020 | Mechoulam et al. | |
| 2020/0138704 A1 | 5/2020 | Wan et al. | |
| 2020/0138721 A1 | 5/2020 | Grother et al. | |
| 2020/0138730 A1 | 5/2020 | Madwar et al. | |
| 2020/0170933 A1 | 6/2020 | Wong et al. | |
| 2020/0190215 A1 | 6/2020 | Schwaeble et al. | |
| 2020/0197364 A1 | 6/2020 | Prud'Homme et al. | |
| 2020/0222402 A1 | 7/2020 | Purohit et al. | |
| 2020/0222529 A1 | 7/2020 | Zhang | |
| 2020/0237733 A1 | 7/2020 | Geissler et al. | |
| 2020/0253875 A1 | 8/2020 | Coffman et al. | |
| 2020/0268667 A1 | 8/2020 | McLaughlin et al. | |
| 2020/0268668 A1 | 8/2020 | McLaughlin et al. | |
| 2020/0268676 A1 | 8/2020 | McLaughlin et al. | |
| 2020/0268677 A1 | 8/2020 | McLaughlin et al. | |
| 2020/0316025 A1 | 10/2020 | Sreedharala et al. | |
| 2020/0330423 A1 | 10/2020 | Brunn et al. | |
| 2020/0330425 A1 | 10/2020 | Bruun et al. | |
| 2020/0368197 A1 | 11/2020 | Donaduzzi et al. | |
| 2020/0383969 A1 | 12/2020 | Coric et al. | |
| 2020/0390704 A1 | 12/2020 | McLaughlin et al. | |
| 2021/0000814 A1 | 1/2021 | Coric et al. | |
| 2021/0008191 A1 | 1/2021 | Conlan et al. | |
| 2021/0267934 A1 | 9/2021 | MacPhail et al. | |

FOREIGN PATENT DOCUMENTS

| | | | |
|---|---|---|---|
| EP | 1 171 134 A1 | 1/2002 | |
| EP | 2 722 036 A1 | 4/2014 | |
| EP | 2 428 202 B1 | 7/2015 | |
| EP | 3 479 822 A1 | 5/2019 | |
| GB | 1 548 022 | 7/1979 | |
| JP | 2017-155049 | 9/2017 | |
| JP | 2017155049 A * | 9/2017 | |
| WO | WO 00/54777 A1 | 9/2000 | |
| WO | WO 2013/165468 A1 | 11/2013 | |
| WO | WO-2013165468 A1 * | 11/2013 | A61K 9/2013 |
| WO | WO 2016/014454 A1 | 1/2016 | |
| WO | WO 2018/082814 A1 | 5/2018 | |
| WO | WO 2018/222923 A1 | 12/2018 | |
| WO | WO 2019/042247 A1 | 3/2019 | |
| WO | WO 2019/153064 A1 | 8/2019 | |
| WO | WO 2019/219773 A1 | 11/2019 | |

(56) References Cited

FOREIGN PATENT DOCUMENTS

| | | |
|---|---|---|
| WO | WO 2019/231225 A1 | 12/2019 |
| WO | WO 2019/231865 A1 | 12/2019 |
| WO | WO-2019232783 A1 * | 12/2019 |
| WO | WO 2020/024011 A1 | 2/2020 |
| WO | WO 2020/037152 A1 | 2/2020 |
| WO | WO 2020/051371 A2 | 3/2020 |
| WO | WO 2020/061584 A1 | 3/2020 |
| WO | WO 2020/098774 A1 | 5/2020 |
| WO | WO 2020/121326 A1 | 6/2020 |
| WO | WO 2020/146753 A1 | 7/2020 |
| WO | WO 2020/165407 A1 | 8/2020 |
| WO | WO 2020/171727 A2 | 8/2020 |
| WO | WO 2020/185214 A1 | 9/2020 |
| WO | WO 2020/186010 A1 | 9/2020 |
| WO | WO 2020/188568 A1 | 9/2020 |

OTHER PUBLICATIONS

"Tablet," Stedman's Medical Dictionary (1995), 26th ed, pp. 1757-1758.

"Tablet," Stedman's Medical Dictionary (2006), 28th ed, pp. 1930-1931.

Seager, H. "Drug-delivery Productsand the Zydis Fast-dissolving Dosage Form," J. Pharm. Pharmacol. 1998, 50: 375-385.

Hu, S. et al. "A mussel-inspired film for adhesion to wet buccal tissue and efficient buccal drug delivery," Nature Communications, 12:1689 (2021).

Alaia et al., "Buccally Absorbed Cannabidiol Shows Significantly Superior Pain Control and Improved Satisfaction Immediately After Rotator Cuff Repair," The American Journal of Sports Medicine 1-8 (2022).

Notcutt, W. et al., "Initial experiences with medicinal extracts of cannabis for chronic pain: Results from 34 'N of 1' studies," Anaesthesia, 2004, 59, pp. 440-452.

Millar, S.A. et al., "A systematic review of cannabidiol dosing in clinical populations," British Journal of Clinical Pharmacology, 2019, 85, pp. 1888-1900.

Ability FDA Label, Otsuka Pharmaceutical Co., Ltd., 2014.

Epidiolex FDA label, Greenwich Biosciences, Inc., 2021.

International Search Report and Written Opinion dated Jan. 28, 2022 in PCT/US21/58045 filed Nov. 4, 2021, 6 pages.

International Search Report and Written Opinion dated Mar. 8, 2022 in PCT/US21/57915 filed Nov. 3, 2021, 12 pages.

International Search Report and Written Opinion dated Jan. 31, 2022 in PCT/US21/58061 filed Nov. 4, 2021, 9 pages.

International Search Report and Written Opinion dated Feb. 4, 2022 in PCT/US21/59184 filed Nov. 12, 2021, 9 pages.

International Search Report and Written Opinion dated Feb. 8, 2022 in PCT/US21/59088 filed Nov. 12, 2021, 13 pages.

Kasteler et al. "Low-dose methotrexate administered weekly is an effective corticosteroid-sparing agent for the treatment of the cutaneous manifestations of dermatomyositis," Journal of the American Academy of Dermatology, vol. 36. Issue 1. (1997) pp. 67-71, [Retrieved on Jan. 10, 2022], Retrieved from <URL:https://sci-hub.se/10.1016/s0190-9622(97)70327-x>.

Baghdadi, "Effect of methotrexate use on the development of type 2 diabetes in rheumatoid arthritis patients: A systematic review and meta-analysis." PLOS ONE, vol. 15(7):e0235637. Jul. 6, 2020 (Jul. 6, 2020) [Retrieved on Jan. 10, 2022], Retrieved from <URL:https://doi.org/10.1371/journal.pone.0235637>.

"Why Do I Need Folic Acid When I'm Taking Methotrexate?" (Evans) Oct. 8, 2020 (Oct. 8, 2020), [Retrieved on Jan. 10, 2022], Retrieved from <URL:https://www.goodrx.com/methotrexate/why-do-i-need-folic-acid-when-taking-methotrexate>.

International Search Report and Written Opinion dated Feb. 1, 2022 in PCT/US21/57938 filed Nov. 3, 2021, 9 pages.

International Search Report and Written Opinion dated Jan. 31, 2022 in PCT/US21/57901 filed Nov. 3, 2021, 11 pages.

"Gelatin vs. Veggie Capsules & CBD", Millie, Oct. 9, 2020, 4 pages, Retrieved from <URL: https://millie.co/blogs/cbd/gelatin-vs-veggie-capsules-cbd>.

International Search Report and Written Opinion dated Feb. 10, 2022 in PCT/US21/58038 filed Nov. 4, 2021, 13 pages.

Chandrasekhar et al., "The role of formulation excipients in the development of lyophilised fast-disintegrating tablets", European Journal of Pharmaceutics and Biopharmaceutics, vol. 72 Issue 1 (Dec. 3, 2008): pp. 119-129.

Augusto dos Santos Garcia et al., "Gelatin/starch orally disintegrating films as a promising system for vitamin C delivery", Food Hydrocolloids, vol. 79 (2018): pp. 127-135.

International Search Report and Written Opinion dated Jan. 31, 2022 in PCT/US21/57931 filed Nov. 3, 2021, 13 pages.

International Search Report and Written Opinion dated Feb. 16, 2022 in PCT/US21/57917 filed Nov. 3, 2021, 11 pages.

International Search Report and Written Opinion dated Mar. 10, 2022 in PCT/US21/059140 filed Nov. 12, 2021, 11 pages.

Seager H, "Drug-delivery Products and the Zydis Fast-dissolving Dosage Form", J Pharm Pharmacol, 1998, 50, pp. 375-382.

Damle B et al., "Pharmacokinetics of a Novel Orodispersible Tablet of Sildenafil in Healthy Subjects", Clinical Therapeutics, vol. 36, No. 2, 2014, pp. 236-244.

Zhu et al., "An evaluation of anti-hyperalgesic effects of cannabidiolic acid-methyl ester in a preclinical model of peripheral neuropathic pain", British Journal of Pharmacology, vol. 177, pp. 2712-2725. (Year: 2020).

Lu et al., "An Introduction to the Endogenous Cannabinoid System", Biological Psychiatry, 2016, 36 pages.

Guindon et al., "The endocannabinoid system and pain", CNS Neurol Disord Drug Targets, 2009; 8 (6), 39 pages.

Bergamaschi et al., "Safety and side effects of cannabidiol, a *Cannabis sativa* constituent", Current Drug Safety, 2011; 6, pp. 237-249.

Iffland et al., "An update on safety and side effects of cannabidiol: a review of clinical data and relevant animal studies", Cannabis and Cannabinoid Research, (2017) 2:1, pp. 139-154.

Zhornitsky et al., "Cannabidiol in humans—the quest for therapeutic targets", Pharmaceuticals, 2012; 5(5), pp. 529-552.

Parker et al., "Regulation of nausea and vomiting by cannabinoids", British Journal of Pharmacology, 2011; 163(7), pp. 1411-1422.

\* cited by examiner

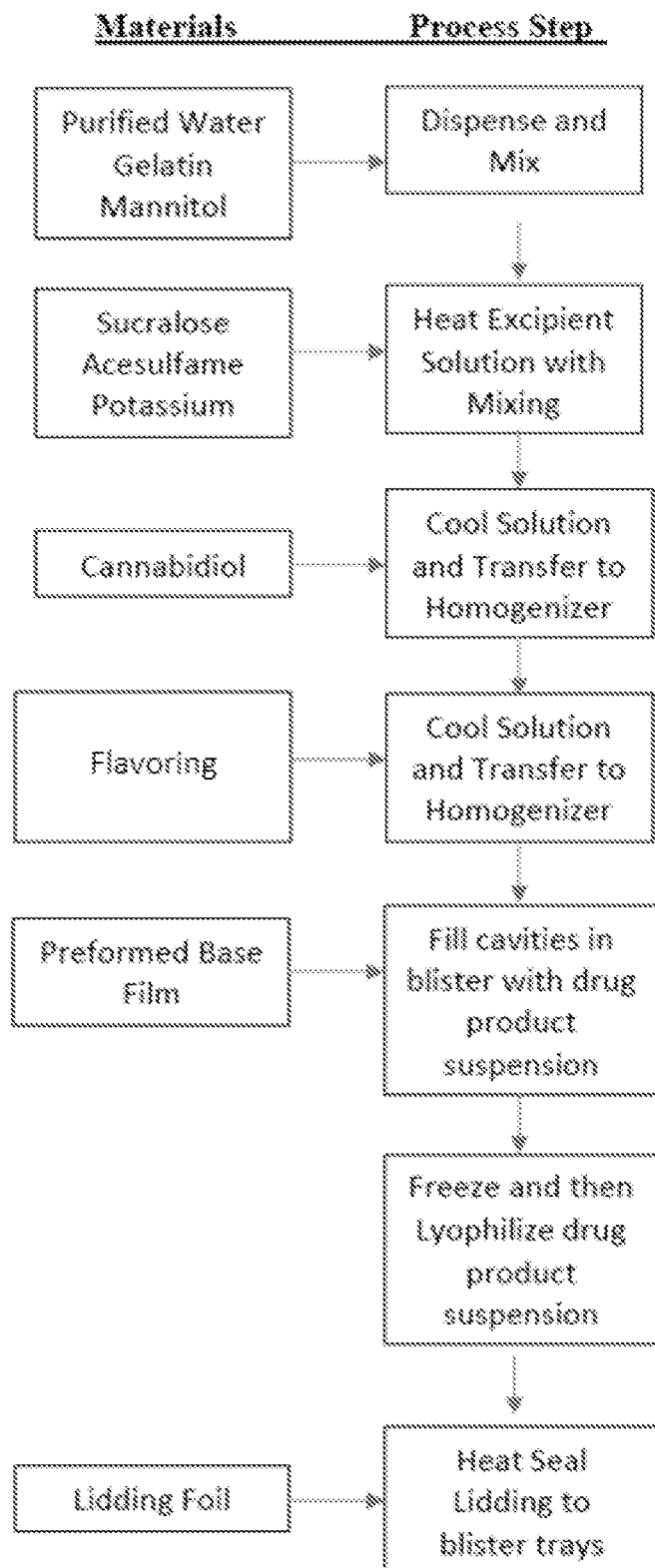

RAPIDLY INFUSING PLATFORM AND COMPOSITIONS FOR THERAPEUTIC TREATMENT IN HUMANS

BACKGROUND OF THE INVENTION

Technical Field

The present disclosure relates to a rapidly infusing platform and compositions for oral mucosal uptake, in particular, treatment of pain, formulated with cannabidiol (CBD) or a derivative/analog thereof as the active therapeutic ingredient (ATI).

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Pain is one of the most common reasons for a patient to seek medical care. There are three general classes of pain: nociceptive pain, psychogenic pain, and neuropathic pain.

In nociceptive pain, the stimulation of the sensory nerve endings called nociceptors causes the sensation of pain. Such pain often occurs after injury or surgery, where the pain signals are transmitted by the nociceptors to the brain. Often, the pain is localized, constant, and has an aching or throbbing quality. Nociceptive pain is treated through the gastrointestinal system with opioid and non-steroidal anti-inflammatory drugs (NSAIDs), and once the damage to the tissue heals, the pain usually resolves or is mitigated upon onset (approximately 25 or more minutes after gastric uptake).

Psychogenic pain is a pain disorder that is associated with psychological factors, for example, some types of mental or emotional problems are the cause of pain or can increase or prolong the pain. Headaches, muscle pains, back pain, and stomach pains are some of the most common types of psychogenic pain. People with this pain disorder have real pain, but the diagnosis is typically made when all physical causes of pain are ruled out.

Neuropathic pain is defined as pain caused by a lesion or disease of the somatosensory nervous system, including peripheral fibers and central neurons. The pain may be triggered by an injury but not necessarily by an injury of the nervous system itself. Neuropathic pain may be acute or chronic, and depending on whether the peripheral or central nervous system is affected, may be categorized as peripheral neuropathic pain or central neuropathic pain. Neuropathic pain is generally characterized by the following clinical features (Teng and Mekhail Pain Practice 3:8-12, 2003, Rajbhandari et al. Pain, 83:627-629, 1999, Melzack et al. Ann. NY. Acad. Sci., 933: 157-174, 2001—each incorporated herein by reference in its entirety): i) there is the presence of an abnormal, unpleasant sensation (dysesthesia) that frequently has a burning or electrical quality with an occasional paroxysmal, brief, shooting, or stabbing quality; ii) although the onset of most neuropathic pain is within days after the precipitating injury, there is no absolute temporal relationship to the originating neural trauma such that it can begin weeks, months, or even years later; iii) pain may be felt in a region of sensory deficit; iv) non-noxious stimuli may be painful (allodynia); v) noxious stimuli may produce greater than normal response (hyperalgesia); and vi) there may be an increase in the intensity of pain with repeated stimuli and the pain may persist after the removal of stimuli.

Although there are numerous available therapies for pain caused by stimulation of the nociceptors, especially treatment with opioid and non-steroidal anti-inflammatory drugs (NSAIDs), neuropathic pain is an area of largely unmet therapeutic need. Due to the distinct pathophysiochemical mechanisms and clinical manifestations associated with neuropathic pain relative to nociceptive pain, agents useful in the treatment of nociceptive pain tend to have reduced effectiveness in neuropathic pain treatment. In particular, the effectiveness of opioids in the treatment of neuropathic pain is diminished relative to their use in the treatment of pain caused as a result of nociceptor stimulation. Due to the diminished effects of opioids in subjects suffering from neuropathic pain, the use of opioids is often frequent and sustained. This over use is often associated with addiction, the development of tolerance, and an increase in the number and severity of side effects associated with opioid use (e.g., euphoric effects, emetic effects, spastic constipation, etc.).

Opioid addiction, widely recognized as a public health emergency, is thus a major difficulty facing clinicians managing patients afflicted with intractable pain types. In fact, of those addicted to opioids, 63.6% reported that pain was the reason for their misuse (Substance Abuse and Mental Health Services Administration. 2017. Results from the 2016 *National Survey on Drug Use and Health* (NSDUH): Detailed Tables. Table 1.28A and 1.28B—incorporated herein by reference in its entirety). With clinical guidelines now encouraging opioid sparing, patients suffering from difficult-to-manage pain varieties, such as neuropathic pain, are left with fewer options than ever. Physicians, patients, and regulatory bodies such as the Food and Drug Administration (FDA) and the Department of Health and Human Services (HHS) are thus seeking new approaches to treatment of various pain conditions.

The Endocannabinoid System (ECS) is a neuromodulatory system comprised of the CB1 and CB2 cannabinoid receptors, endogenous cannabinoid ligands known as Endocannabinoids, and the enzymes responsible for the synthesis and degradation of cannabinoids. The ECS is involved in regulating the inflammatory response to injury, as well as modulating pain, and thus is a proposed pharmacological target for pain management. Cannabidiol (CBD) is a non-intoxicating cannabinoid that has garnered interest as a pain therapeutic. Furthermore, in 2018, the United States Congress passed the 2018 Farm Bill, which legalized Industrial Hemp—*Cannabis sativa* L. plants containing<0.3% of tetrahydrocannabinol (THC)—and its derivative cannabinoids, including CBD.

However, scientific validation of CBD as an effective pain therapeutic has remained elusive, and there is currently no high-quality evidence that CBD itself (e.g., without THC) is useful for the treatment of pain. In fact, in September 2019, the Federal Trade Commission (FTC) wrote warning letters cautioning CBD suppliers against deceptive advertisements and marketing claims regarding the use of CBD for treating pain, stating that such claims are not sufficiently supported by scientific evidence via well-controlled human clinical trials.

The following disadvantages have contributed to the current lack of scientific evidence supporting the use of CBD for the treatment of pain:
1) administration of CBD has historically relied upon impure *cannabis* preparations—such as decoctions which could then be swallowed, or through inhalation of the vapors of *cannabis* by smoking the dried plant material—which may contain unknown or non-standardized amounts of CBD, other active ingredients such as THC, as well as other potential toxins. Smoking, in particular, is an undesirable route of administration as the patient must inhale unhealthy tars and associated carcinogens into their lungs, often for prolonged periods of time;

2) inaccurate dosing, for example, tinctures and other liquid dosage forms applied via droppers, sprayers, and the like are imprecise and an inaccurate, often leading to discrepancies in data collection and inconsistent outcomes;

3) difficult administration and patient intolerability, for example, the oily and foul taste of CBD results in an unpleasant user experience and poor patient compliance when administered orally; and 4) low bioavailability resulting in low and inconsistent levels of CBD in systemic circulation. Specifically, drugs taken by mouth and swallowed are absorbed first into the blood perfusing the gastrointestinal (GI) tract. The venous drainage from the GI tract is into the blood perfusing the liver, and thus drugs absorbed from the lumen of GI tract are immediately presented to the liver—the major detoxifying organ of the body— whereby the drugs are metabolized and then returned to the left side of the heart via the hepatic portal vein and sent into systemic circulation. This first pass metabolism through the liver may result in the removal of a substantial proportion of an ingested drug, and is more pronounced for some drugs than others; in the case of cannabinoids such as CBD, extensive first pass metabolism provides a paltry bioavailability of only about 6 to 11% when ingested orally.

Patient intolerability is a particular problem for pain therapy when one considers that treatment often involves repetitive and prolonged treatment, for example, subjects suffering from certain types of pain may require therapeutic relief two, three, four, etc. times a day for weeks or months on end. Therefore, patient compliance in terms of prolonged usage for extended pain treatment is a major hurdle for foul-tasting therapeutics such as CBD.

SUMMARY OF THE INVENTION

In view of the forgoing, there exists a need for new pain treatment methods based on non-opioid active therapeutic ingredients (ATIs) which can be presented through a rapidly infusing platform in bioavailable unit dosage form for accurate dosing, easy administration, high levels of patient compliance, and which provide a rapid onset of therapeutic pain relief.

Accordingly, it is an object of the present invention to provide novel methods of treating pain in a subject meeting the above criteria.

This and other objects, which will become apparent during the following detailed description, have been achieved by the inventors' discovery of a platform through which CBD or a derivative/analog thereof can be successfully formulated into a lyophilized, rapidly infusing composition using gelatin and a sugar alcohol as a pharmaceutically acceptable binder and/or excipient system with a rapid disintegrating profile for oral mucosal administration.

Thus, the present invention provides:

(1) A method of treating pain in a subject, comprising: administering to the subject in need thereof, via the oral mucosa, a rapidly infusing composition comprising (a) a pharmaceutically acceptable binder and/or excipient system comprising gelatin and a sugar alcohol, and (b) a therapeutically effective amount cannabidiol (CBD) or a derivative/analog thereof.

(2) The method of (1), wherein the rapidly infusing composition is lyophilized.

(3) The method of (1) or (2), wherein the rapidly infusing composition has a disintegration time of approximately 1 to 30 seconds in deionized water maintained at 37° C.±2° C.

(4) The method of any one of (1) or (3), wherein the rapidly infusing composition has a disintegration time of approximately 1 to 5 seconds in deionized water maintained at 37° C.±2° C.

(5) The method of any one of (1) to (4), wherein the gelatin is present in the rapidly infusing composition in an amount of 10 to 35 wt. %, based on a total weight of the rapidly infusing composition on a dry basis.

(6) The method of any one of (1) to (5), wherein the sugar alcohol is present in the rapidly infusing composition in an amount of 5 to 35 wt. %, based on a total weight of the rapidly infusing composition on a dry basis.

(7) The method of any one of (1) to (6), wherein the sugar alcohol comprises mannitol.

(8) The method of any one of (1) to (7), wherein the CBD or derivative/analog thereof is present in the rapidly infusing composition in an amount of 20 to 70 wt. %, based on a total weight of the rapidly infusing composition on a dry basis.

(9) The method of any one of (1) to (8), wherein the rapidly infusing composition is formulated with a solid form of the CBD.

(10) The method of any one of (1) to (9), wherein the rapidly infusing composition is formulated with a solid form of the CBD having a purity between 95 and 99.9 wt. %.

(11) The method of any one of (1) to (10), wherein the rapidly infusing composition is formulated with a solid form of the CBD that has been micronized to have a D50 diameter between 1 and 50 μm.

(12) The method of any one of (1) to (11), wherein the rapidly infusing composition further comprises at least one selected from the group consisting of a sweetener, a flavorant, and a colorant.

(13) The method of any one of (1) to (12), wherein the rapidly infusing composition is administered to the subject via the buccal mucosa.

(14) The method of any one of (1) to (13), wherein the therapeutically effective amount of CBD or derivative/analog thereof is from 10 to 100 mg of CBD per dose.

(15) The method of any one of (1) to (14), wherein the rapidly infusing composition is administered to the subject 1 to 10 times per day.

(16) The method of any one of (1) to (15), wherein the subject is a human.

(17) The method of any one of (1) to (16), wherein the pain is neuropathic pain.

(18) The method of any one of (1) to (17), wherein the pain is acute neuropathic pain.

(19) The method of any one of (1) to (18), wherein the pain is postsurgical pain and the rapidly infusing composition is administered post-operatively to the subject who has undergone a surgical procedure.

(20) The method of (19), wherein the surgical procedure is knee arthroplasty.

(21) The method of (19), wherein surgical procedure is shoulder arthroscopy.

(22) The method of any one of (1) to (19), wherein the subject has cancer and the pain is cancer-associated pain.

(23) The method of any one of (1) to (19), or (22) wherein the subject has pancreatic cancer and the pain is pancreatic cancer-associated pain.

(24) The method of any one of (1) to (23), wherein the rapidly infusing composition is formulated with a CBD derivative/analog.

(25) The method of (24), wherein the CBD derivative/analog is cannabidiolic acid methyl ester.

(26) A rapidly infusing composition, comprising:
gelatin, in an amount of 10 to 35 wt. %, based on a total weight of the rapidly infusing composition on a dry basis;
a sugar alcohol, in an amount of 5 to 35 wt. %, based on a total weight of the rapidly infusing composition on a dry basis;
cannabidiol (CBD) or a derivative/analog thereof, in an amount of 20 to 70 wt. %, based on a total weight of the rapidly infusing composition on a dry basis.

(27) The rapidly infusing composition of (26), wherein the rapidly infusing composition is lyophilized.

(28) The rapidly infusing composition of (26) or (27), wherein the rapidly infusing composition has a disintegration time of approximately 1 to 30 seconds in deionized water maintained at 37° C.±2° C.

(29) The rapidly infusing composition of any one of (26) to (28), wherein the rapidly infusing composition has a disintegration time of approximately 1 to 5 seconds in deionized water maintained at 37° C.±2° C.

(30) The rapidly infusing composition of any one of (26) to (29), wherein the sugar alcohol comprises mannitol.

(31) The rapidly infusing composition of any one of (26) to (30), wherein the rapidly infusing composition further comprises at least one selected from the group consisting of a sweetener, a flavorant, and a colorant.

(32) The rapidly infusing composition of (31), wherein the rapidly infusing composition comprises the flavorant, and the flavorant comprises lemon-lime flavor.

(33) The rapidly infusing composition of (31) or (32), wherein the rapidly infusing composition comprises the colorant, and the colorant comprises FD&C Yellow #5.

(34) The rapidly infusing composition of any one of (26) to (33), wherein the rapidly infusing composition is formulated with a solid form of the CBD.

(35) The rapidly infusing composition of any one of (26) to (34), wherein the rapidly infusing composition is formulated with a solid form of the CBD having a purity between 95 and 99.9 wt. %.

(36) The rapidly infusing composition of any one of (26) to (35), wherein the rapidly infusing composition is formulated with a solid form of the CBD that has been micronized to have a D50 diameter between 1 and 50 μm.

(37) The rapidly infusing composition of any one of (26) to (36), further comprising melatonin.

(38) The rapidly infusing composition of any one of (26) to (37), wherein the rapidly infusing composition is formulated with a CBD derivative/analog.

(39) The rapidly infusing composition of (38), wherein the CBD derivative/analog is cannabidiolic acid methyl ester.

BRIEF DESCRIPTION OF THE DRAWINGS

The foregoing paragraphs have been provided by way of general introduction, and are not intended to limit the scope of the following claims. The described embodiments, together with further advantages, will be best understood by reference to the following detailed description when considered in conjunction with the accompanying drawing, wherein:

The FIGURE illustrates a process flow diagram for the manufacture of a lyophilized rapidly infusing composition.

DETAILED DESCRIPTION OF THE INVENTION

In the following description, it is understood that other embodiments may be utilized and structural and operational changes may be made without departure from the scope of the present embodiments disclosed herein.

Definitions

As used herein, the terms "compound", "complex", and "product" are used interchangeably, and are intended to refer to a chemical entity, whether in the solid, liquid or gaseous phase, and whether in a crude mixture or purified and isolated. Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present, and all such stable isomers are contemplated in the present disclosure. Cis- and trans- (or E- and Z-) geometric isomers, when present, may be isolated as a mixture of isomers or as separated isomeric forms. Compounds referenced in the disclosure can be isolated in optically active or racemic forms. Optically active forms may be prepared by resolution of racemic forms or by synthesis from optically active starting materials. All processes used to prepare these compounds and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions, the end products referenced in the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds may be separated into the individual isomers. Compounds referenced in the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "solvate" refers to a physical association of a referenced compound with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvent molecules which may form the solvate include, but are not limited to, water, methanol, ethanol, n-propanol, isopropanol, butanol, isobutanol, tert-butanol, ethyl acetate and other lower alkanols, glycerin, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, commensurate with a reasonable benefit/risk ratio.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids and phenols. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990)—which is incorporated herein by reference in its entirety.

When referencing a particular composition/material, the phrase "consists essentially of", means that the particular composition/material may include minor amounts of impurities so long as those impurities do not affect the basic and novel property of the invention the ability to treat pain.

As used herein, the terms "optional" or "optionally" means that the subsequently described event(s) can or cannot occur or the subsequently described component(s) may or may not be present (e.g., 0 wt. %).

As used herein, the terms "treat", "treatment", and "treating" in the context of the administration of a therapy to a subject in need thereof refers to the reduction or amelioration of severity of symptoms of the condition being treated; reduction of duration of symptoms of the condition being treated; reduction, inhibition, slowing, or arresting of the progression of symptoms associated with the condition; reduction of frequency of symptoms of the condition being treated; elimination of symptoms and/or underlying cause of the condition; prevention of the occurrence of symptoms of the condition, for example in a subject that may be predisposed to the condition but does not yet experience or exhibit symptoms of the condition; improvement or remediation or amelioration of damage following a condition, for example improving, remediating, or ameliorating inflammation; and/or causing regression of the condition.

The term "pain" should be understood to include any unpleasant sensory and emotional experience associated with actual or potential tissue damage, or described in terms of such damage. This term generally includes nociceptive pain, neuropathic pain, and psychogenic pain; including any subset of pain associated therewith such as phantom pain, breakthrough pain, incident pain, inflammatory pain, post-surgical (postoperative) pain, cancer-associated pain, peripheral pain, central pain, spastic pain, and the like; as well as both acute pain and chronic pain conditions.

The term "subject" and "patient" are used interchangeably. As used herein, they refer to any subject for whom or which therapy is desired. In most embodiments, the subject is a human.

The terms "administer", "administering", "administration", and the like, as used herein, refer to the methods that may be used to enable delivery of the active therapeutic ingredient (ATI) to the desired site of biological action. Routes or modes of administration are as set forth herein.

The term "Rapid Infusion Technology™ (RITe) platform" or "rapidly infusing composition", as used herein means a solid dosage form containing medicinal substances that disintegrates rapidly in the oral cavity (when contacted with saliva) with no need for chewing or drinking liquids to ingest these medicinal substances, with an in-vitro disintegration time of 30 second or less according to the United States Pharmacopeia (USP)<701> Disintegration Test. The disclosed rapidly infusing compositions are thus a different dosage form than, for example, a chewable tablet, a lozenge intended to be dissolved slowly in the mouth, an orally disintegrating film or tablet designed to be dissolved/disintegrated in the mouth and swallowed (also called "orodispersible" formulations), a tablet that should be swallowed whole with food or liquid, or any other oral dosage form designed for absorption from the GI tract.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount" or "therapeutically effective amount" refer to a sufficient amount of an active therapeutic ingredient (ATI) being administered which provides the desired therapeutic or physiological effect or outcome, for example, the amount of ATI sufficient for relieving to some extent one or more of the pain symptoms of the condition being treated. The result can be a reduction and/or alleviation of the signs, symptoms, or causes of a disease, or any other desired alteration of a biological system. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the age and general condition of the subject, mode of administration, and the like. An appropriate "effective amount" in any individual case may be determined by one of ordinary skill in the art using only routine experimentation, for example through the use of dose escalation studies.

Rapid Infusion Technology™ (RITe) Platform

The present disclosure provides a therapeutic formulation presented in the form of a rapidly infusing composition which is suitable for administration of lipophilic active therapeutic ingredients (ATIs) such as cannabidiol (CBD) via a non-gastric mucosal surface. As described in more detail below, the novel delivery platform allows otherwise difficult to formulate ATIs—such as CBD—to be presented in unit dosage form for accurate dosing and in an easy-to-take format for high levels of patient compliance. For example, the rapidly infusing composition may be presented in tablet form and packaged in individual blister units.

In particular, the rapidly infusing composition enables oral mucosal administration of lipophilic ATIs in a solid dosage form directly into systemic circulation via the sublingual mucosa or the buccal mucosa and avoidance of first pass metabolism. The rapidly infusing composition thus presents lipophilic ATIs such as CBD, which may be susceptible to extensive first pass metabolism, in a highly bioavailable dosage form. For example, CBD administered via the rapidly infusing delivery platform herein may have a bioavailability of at least 50%, preferably at least 55%, preferably at least 60%, preferably at least 65%, preferably at least 70%, preferably at least 75%, preferably at least 80%, preferably at least 85%, preferably at least 90%, and up to 99%, preferably up to 98%, preferably up to 96%, preferably up to 95%, preferably up to 92%.

Administration may carried out by simply placing the rapidly infusing composition directly in the buccal cavity (between the cheek and gum) or over the sublingual mucous gland (under the ventral surface of the tongue). Preferred rapidly infusing compositions are those which are lyophilized products formulated for rapid disintegration when placed in such an oral environment for rapid release of the ATI. The rapidly infusing compositions of the present disclosure may have a disintegration time of from approximately 1 second to 30 seconds or less, preferably 25 seconds or less, preferably 20 seconds or less, preferably 15 seconds or less, preferably 10 seconds or less, preferably 5 seconds or less, preferably 3 seconds or less, according to the United States Pharmacopeia (USP)<701> Disintegration Test performed in deionized water maintained at 37° C.±2°. In particular, preferred rapidly infusing compositions are those formulated for oral disintegration in 5 seconds or less, preferably 4 seconds or less, preferably 3 seconds or less, preferably 2 seconds or less, preferably in approximately 1 second, according to the United States Pharmacopeia (USP) <701> Disintegration Test performed in deionized water maintained at 37° C.±2°. A disintegration profile no higher than the above-mentioned upper limit when in intimate contact with a non-gastric mucosal surface provides for rapid absorption of the ATI and short onset times to therapeutic relief. Also, patient compliance may be improved, particularly in terms of temporary abstinence from swallowing, which is often triggered when a patient is presented with foul-tasting oral medications. Any issues related to foul taste may be minimized with the above rapid disintegration times, which reduces the tendency for enteral oral administration through voluntary or involuntary swallowing, and as a result, the aforementioned high levels of bioavailability may be achieved.

The rapid disintegration profile disclosed herein, coupled with the direct introduction of the ATI into systemic circulation through the sublingual mucosa or the buccal mucosa, preferably through the buccal mucosa, provides a rapid onset of therapeutic effect. For example, the rapidly infusing composition may provide the desired pain-reduction effects in (has an onset time of) under 15 minutes, preferably under 10 minutes, preferably under 5 minutes, preferably under 4 minutes, preferably under 3 minutes, preferably under 2 minutes, preferably under 1 minute, preferably under 45 seconds, preferably under 30 seconds, preferably under 20 seconds, preferably under 10 seconds, preferably approximately 5 seconds. Such short onset times are superior to those which can be obtained with traditional orally disintegrating tablets made through compression tabletting.

The rapidly infusing composition herein generally contains (a) a pharmaceutically acceptable binder and/or excipient system that includes gelatin and a sugar alcohol e.g., mannitol, and optionally one or more of a sweetener, a flavorant, and a colorant; and (b) a therapeutically effective amount of an active therapeutic ingredient such as cannabidiol (CBD) or a pharmaceutically acceptable derivative/analog, salt, or solvate thereof Pharmaceutically Acceptable Carrier and/or Excipient System Carriers and/or excipients are ingredients which do not provide a therapeutic effect themselves, but which are designed to interact with, and enhance the properties of, the active therapeutic ingredient. In particular, carriers and/or excipients may act as a vehicle for transporting the active therapeutic ingredient from one organ, or portion of the body, to another organ, or portion of the body. The selection of appropriate carrier/excipient ingredients may impact the solubility, distribution, release profile/kinetics, absorption, serum stability, therapeutic onset time, and ultimately the efficacy of the ATI, as well as the shelf-life, dosage forms, and processability of the drug product. Each ingredient in the pharmaceutically acceptable carrier and/or excipient system must be "pharmaceutically acceptable" in the sense of being compatible with the other ingredients of the rapidly infusing composition and not injurious to the patient.

In light of the above, particular preference is given herein to pharmaceutically acceptable carrier and/or excipient systems which include gelatin and a sugar alcohol (e.g., mannitol).

Gelatin is to be included in the pharmaceutically acceptable carrier and/or excipient system in order to effect matrix formation in the lyophilized product, i.e., gelatin may act primarily as a matrix former. During manufacture of the rapidly infusing composition, lyophilization from an aqueous suspension results in the removal of water thereby leaving behind a gelatin matrix/scaffolding upon which the ATI can be evenly dispersed or suspended. It has been found that gelatin has a propensity to establish a stable matrix in lyophilized form, yet allow for rapid disintegration when brought into contact with the aqueous oral environment, thereby providing efficient transfer of the ATI from the hydrophilic vehicle to the oral mucosa. In this regard, bovine gelatins are preferred.

The amount of gelatin used may be varied. Generally, gelatin may be present in the rapidly infusing composition in an amount of at least 10 wt. %, preferably 12 wt. %, preferably 14 wt. %, preferably 16 wt. %, preferably 18 wt. %, preferably 20 wt. %, preferably 22 wt. %, and up to 35 wt. %, preferably up to 32 wt. %, preferably up to 30 wt. %, preferably up to 28 wt. %, preferably up to 26 wt. %, preferably up to 24 wt. %, based on a total weight of the rapidly infusing composition on a dry basis.

The pharmaceutically acceptable carrier and/or excipient system is also formulated with one or more sugar alcohols, which may act primarily as a bulking agent. Examples of sugar alcohols include, but are not limited to, erythritol, xylitol, sorbitol, maltitol, mannitol, lactitol, and glycerin, which may be used singly or in combinations. Advantage can also be taken of the effect of certain sugar alcohols in terms of taste (sweetness and coolness due to endothermal heat of solution), as well as their ability to aid/speed tablet disintegration. In this regard, particular preference is given to mannitol.

The sugar alcohol, preferably mannitol, may be present in the rapidly infusing composition in any amount which provides the desired bulking/taste/disintegration effects. Generally, this amount will range from of at least 5 wt. %, preferably at least 10 wt. %, preferably at least 12 wt. %, preferably at least 14 wt. %, preferably at least 16 wt. %, preferably at least 18 wt. %, and up to 35 wt. %, preferably up to 30 wt. %, preferably up to 28 wt. %, preferably up to 26 wt. %, preferably up to 24 wt. %, preferably up to 22 wt. %, preferably up to 20 wt. %, based on a total weight of the rapidly infusing composition on a dry basis.

In some embodiments, a weight ratio of gelatin to sugar alcohol ranges from 1:3, preferably from 1:2, preferably from 1:1, preferably from 1.1:1, and up to 3:1, preferably up to 2:1, preferably up to 1.5:1, preferably up to 1.2:1.

The pharmaceutically acceptable carrier and/or excipient system may also optionally include one or more of a sweetener, a flavorant, and a colorant.

The sweetener may be used in any amount which provides the desired sweetening effect, generally in amount of 0 to 5 wt. %, for example in an amount of up to 5 wt. %, preferably up to 4.5 wt. %, preferably up to 4 wt. %, preferably up to 3.5 wt. %, preferably up to 3 wt. %, preferably up to 2.5 wt. %, preferably up to 2 wt. %, preferably up to 1.5 wt. %, preferably up to 1 wt. %, based on a total weight of the rapidly infusing composition on a dry basis. Suitable examples of sweeteners include, but are not limited to, aspartame, saccharin (as sodium, potassium or calcium saccharin), cyclamate (as a sodium, potassium or calcium salt), sucralose, acesulfame-K, thaumatin, neohisperidin, dihydrochalcone, ammoniated glycyrrhizin, dextrose, maltodextrin, fructose, levulose, sucrose, and glucose, which may be used singly or in combinations, with particular preference given to sucralose and acesulfame-K.

It is to be readily appreciated by those of ordinary skill in the art that one or more flavorants may be optionally included in the rapidly infusing composition to mask any unpleasant taste imparted by certain ingredients (e.g., an unpleasant tasting ATI) or to otherwise impart an acceptable taste profile to the composition, and the composition is not limited to any particular flavor. Suitable flavorants include, but are not limited to, oil of wintergreen, oil of peppermint, oil of spearmint, oil of sassafras, oil of clove, cinnamon, anethole, menthol, thymol, eugenol, eucalyptol, lemon, lime, lemon-lime, orange, and other such flavor compounds to add fruit notes (e.g., citrus, cherry etc.), spice notes, etc., to the composition. The flavorants may be constitutionally composed of aldehydes, ketones, esters, acids, alcohols (including both aliphatic and aromatic alcohols), as well as mixtures thereof. Specific mention is made to lemon-lime flavor powder, which works particularly well with CBD as the ATI. The flavorant may be used in any amount which provides the desired flavor, generally in an amount of 0 to 5 wt. %, for example in an amount of up to 5 wt. %, preferably up to 4 wt. %, preferably up to 3 wt. %, preferably up to 2 wt. %, preferably up to L5 wt. %, preferably up to 1 wt. %, preferably up to 0.5 wt. %, preferably up to 0.1 wt. %, based on a total weight of the rapidly infusing composition on a dry basis.

Two main strategies contribute to the taste masking success of the present disclosure. First, any issues related to foul taste are fundamentally mitigated by the short oral residence times provided by the rapid disintegration profile described heretofore. One "takes it and it's gone." Second, when formulated with a flavorant, a robust mixture of flavors will hit the tongue at essentially the same time—the flavor of the CBD still hits the tongue, but the perception of the flavor is canceled or mitigated by the simultaneous arrival of other flavors. Even then, the robust mixture of flavors will quickly subside as the composition is rapidly absorbed through the oral mucosa.

Likewise, the rapidly infusing composition may be colored or tinted through the optional use of one or more colorants. Suitable colorants are those approved by appropriate regulatory bodies such as the FDA and those listed in the European Food and Pharmaceutical.

Directives and include both pigments and dyes such as FD&C and D&C dyes, with specific mention being made to FD&C Yellow #5.

In addition to gelatin and a sugar alcohol (e.g., mannitol), and optionally one or more of a sweetener, a flavorant, and a colorant, the pharmaceutically acceptable carrier and/or excipient system may optionally include one or more other pharmaceutically acceptable carriers and/or excipients known to those of ordinary skill in art, in art appropriate levels. Examples of which include, but are not limited to, fillers or extenders such as starches (e.g., corn starch and potato starch), sugars (e.g., lactose or milk sugar), high molecular weight polyethylene glycols, silicic acid, aluminum monostearate, polyesters, polycarbonates, and polyanhydrides;

binders, such as cellulose, and its derivatives, (e.g., sodium carboxymethyl cellulose, hydroxypropyl cellulose, hydroxypropylmethyl cellulose, methyl cellulose, ethyl cellulose and cellulose acetate), alginates, polyvinyl pyrrolidone, powdered tragacanth, malt, and acacia;

disintegrating agents, such as agar-agar, calcium carbonate, tapioca starch, alginic acid, certain silicates, sodium carbonate, sodium starch glycolate, and cross-linked sodium carboxymethyl cellulose;

surfactants/absorption accelerators/wetting agents/emulsifying agents/solubilizers, including any of the anionic, cationic, nonionic, zwitterionic, amphoteric and betaine variety, such as polyalkylene oxide copolymers (e.g., poloxamer), sodium lauryl sulfate, sodium dodecyl benzene sulfonate, sodium docusate, sodium lauryl sulfoacetate, alkali metal or ammonium salts of lauroyl sarcosinate, myristoyl sarcosinate, palmitoyl sarcosinate, stearoyl sarcosinate and oleoyl sarcosinate, cetyl alcohol, glycerol monostearate, polyoxyethylene sorbitol, fatty acid esters of sorbitan, polysorbates (polyalkolyated fatty acid esters of sorbitan) (e.g., polyoxyethylene sorbitan monostearate, monoisostearate and monolaurate), polyethylene oxide condensates of alkyl phenols, cocoamidopropyl betaine, lauramidopropyl betaine, palmityl betaine, glyceryl monooleate, glyceryl monostearate, fatty alcohols (e.g., cetostearyl and cetyl alcohol), medium chain triglycerides, polyethoxylated castor oil, polyethoxylated alkyl ethers (e.g., ethoxylated isostearyl alcohols), polyethylene glycols (Macrogols), polyoxyethylene stearates, anionic and nonionic emulsifying waxes, propylene glycol, and propylene glycol alginates;

absorbents, such as kaolin and bentonite clay;

lubricants, such as talc, calcium stearate, magnesium stearate, solid polyethylene glycols, zinc stearate, sodium stearate, stearic acid, ethyl oleate, and ethyl laurate;

controlled release agents such as cross-linked polyvinyl pyrrolidone (crospovidone);

opacifying agents such as titanium dioxide;

buffering agents such as sodium hydroxide, sodium citrate, magnesium hydroxide, and aluminum hydroxide;

diluents/tableting agents such as dicalcium phosphate;

antioxidants, including (1) water soluble antioxidants, such as ascorbic acid, cysteine hydrochloride, sodium bisulfate, sodium metabisulfite, and sodium sulphite, (2) oil-soluble antioxidants, such as ascorbyl palmitate, butylated hydroxyanisole (BHA), butylated hydroxytoluene (BHT), lecithin, propyl gallate, and alpha-tocopherol; and (3) metal chelating agents, such as citric acid, ethylenediamine tetraacetic acid (EDTA), tartaric acid, and phosphoric acid;

antibacterial and antifungal agents, such as paraben, chlorobutanol, phenol, sorbic acid;

as well as other non-toxic compatible substances employed in pharmaceutical formulations, such as cyclodextrins, liposomes, and micelle forming agents including mixtures thereof.

Preferred rapidly infusing compositions are those which contain less than 1 wt. %, preferably less than 0.5 wt. %, preferably less than 0.1 wt. %, preferably less than 0.05 wt. %, preferably less than 0.001 wt. %, preferably 0 wt. %, of other pharmaceutically acceptable carriers and/or excipients, such as those listed above.

Active Therapeutic Ingredient (ATI)

The amount of active therapeutic ingredient (ATI) which can be combined with the pharmaceutically acceptable carrier and/or excipient system to produce the rapidly infusing composition may vary depending upon the subject being treated, and other factors. The amount of ATI which can be combined with the pharmaceutically acceptable carrier and/or excipient system to produce a single dosage form will generally be that amount which produces a therapeutic effect. Generally, this amount will range from 0.1 to 90 wt. % of ATI, for example, at least 20 wt. %, preferably at least 22 wt. %, preferably at least 24 wt. %, preferably at least 26 wt. %, preferably at least 28 wt. %, preferably at least 30 wt. %, preferably at least 32 wt. %, preferably at least 34 wt. %, preferably at least 36 wt. %, preferably at least 38 wt. %, preferably at least 40 wt. %, preferably at least 42 wt. %, preferably at least 44 wt. %, preferably at least 46 wt. %, preferably at least 48 wt. %, preferably at least 50 wt. %, preferably at least 52 wt. %, preferably at least 54 wt. %, and up to 70 wt. %, preferably up to 68 wt. %, preferably up to 66 wt. %, preferably up to 64 wt. %, preferably up to 62 wt. %, preferably up to 60 wt. %, preferably up to 58 wt. %, preferably up to 56 wt. % of the ATT, based on a total weight of the rapidly infusing composition on a dry basis.

In terms of unit dose, the rapidly infusing composition is generally formulated with 2 to 100 mg of ATI per unit (e.g. tablet), for example at least 2 mg, preferably at least 4 mg, preferably at least 6 mg, preferably at least 8 mg, preferably at least 10 mg, preferably at least 12 mg, preferably at least 14 mg, preferably at least 16 mg, preferably at least 18 mg, preferably at least 20 mg, preferably at least 22 mg, preferably at least 24 mg, and up to 100 mg, preferably up to 75 mg, preferably up to 70 mg, preferably up to 65 mg, preferably up to 60 mg, preferably up to 55 mg, preferably up to 50 mg, preferably up to 45 mg, preferably up to 40 mg, preferably up to 35 mg, preferably up to 30 mg, preferably up to 25 mg of ATI per unit (e.g., tablet).

In preferred embodiments, the rapidly infusing composition is formulated with, as the active therapeutic ingredient, cannabidiol (CBD), or any pharmaceutically acceptable derivative/analog, salt, solvate, or stereoisomer thereof. In some preferred embodiments, CBD or a derivative/analog thereof is the only active therapeutic ingredient in the rapidly infusing composition. In some preferred embodiments, CBD is the only active therapeutic ingredient in the rapidly infusing composition. In some preferred embodiments, a CBD derivative/analog is the only active therapeutic ingredient in the rapidly infusing composition. In other embodiments, CBD or derivative/analog thereof may be combined with other active therapeutic ingredients. For example, CBD, formulated as described below may be combined with a water-soluble ATI such as melatonin, as a sleep aid.

Preferred rapidly infusing compositions are those which are formulated with CBD, preferably a solid form of CBD. That is, the rapidly infusing composition is prepared through lyophilization from a drug product suspension in which the CBD is in the form of a solid. In particular, micronized particles of CBD are preferred. In some embodiments, the rapidly infusing composition is formulated with solid CBD in the form of micronized particles having a D50 particle size in the range of 1 µm to 50 µm, for example, those having a D50 particle size of at least 1 µm, preferably at least 10 µm, preferably at least 20 µm, preferably at least 30 µm, preferably at least 40 µm, and up to 50 µm, preferably up to 40 µm, preferably up to 30 µm, preferably up to 20 µm, preferably up to 10 µm.

Even more preferred are those rapidly infusing compositions which are formulated with a solid form of CBD having a purity of at least 95 wt. %, preferably at least 96 wt. %, preferably at least 97 wt. %, preferably at least 98 wt. %, preferably at least 99 wt. %. While CBD having a purity of 100 wt. % is likely not achievable, preferably rapidly infusing compositions are formulated with a solid form of CBD having a purity up to 99.1 wt. %, preferably up to 99.2 wt. %, preferably up to 99.3 wt. %, preferably up to 99.4 wt. %, preferably up to 99.5 wt. %, preferably up to 99.6 wt %, preferably up to 99.7 wt %, preferably up to 99.8 wt. %, preferably up to 99.9 wt. %. The percent purity of CBD refers to the percent of CBD by mass relative to a total weight of CBD containing material—the CBD containing material being the sum of CBD plus any additional impurities which may be present, such as those impurities originating from the biomass from which the CBD is obtained (e.g., *Cannabis sativa* L./"Industrial Hemp") or encountered during manufacture. The purity may be determined by methods known to those of ordinary skill in the art, for example, one or more of liquid chromatography such as high performance liquid chromatography (HPLC), liquid chromatography-mass spectrometry (LCMS), and liquid chromatography with tandem mass spectrometry (LCMSMS); gas chromatography such as headspace gas chromatography with flame ionization detection (HS-GC-FID), gas chromatography mass spectrometry (GC/NIS), and headspace gas chromatography-mass spectrometry (HSGCMS); inductively coupled plasma-mass spectrometry (ICP-MS); and polymerase chain reaction (PCR).

Examples of potential impurities, such as those originating from the biomass from which the CBD is obtained (e.g., *Cannabis sativa* L./"Industrial Hemp") or encountered during manufacture, include, but are not limited to, cannabinoids (other than CBD) including, but not limited to, cannabidivarin (CBDV), cannabichromene (CBC), cannabidiolic acid (CBDa), cannabigerol (CBG), cannabigerolic acid (CBGa), cannabinol (CBN), tetrahydrocannabinolic acid (THCa), tetrahydrocannabivarin (THCV), tetrahydrocannabivarin acid (THCVa), and tetrahydrocannabinol (Δ9-THC) and related THC-cannabinoids such as Δ8-THC;

pesticides including, but not limited to, aldicarb, carbofuran, chlordane, chlorfenapyr, chlorpyrifos, coumaphos, daminozide, dichlorvos (DDVP), dimethoate, ethoprophos, etofenprox, fenoxycarb, fipronil, imazalil, methiocarb, methyl parathion, paclobutrazol, propoxur, spiroxamine, and thiacloprid;

residual solvents including, but not limited to, 1,4-dioxane, 2-butanol, 2-ethoxyethanol, 1,2-dichloroethane, acetone, acetonitrile, benzene, butane, cumene, cyclohexane, chloroform, ethanol, ethyl acetate, ethyl benzene, ethylene oxide, ethylene glycol, ethyl ether, heptane, isopropanol, methanol, methylene chloride, hexanes, isopropyl acetate, pentanes, propane, toluene, tetrahydrofuran, trichloroethene, and xylenes;

microbials including, but not limited to, *Aspergillus flavus, Aspergillus fumigatus, Aspergillus niger, Aspergillus terreus, Salmonella*, and Shiga toxin-producing *E. coli*;

mycotoxins including, but not limited to, aflatoxins (e.g., aflatoxin B1, aflatoxin B2, aflatoxin G1, and aflatoxin G2) and ochratoxin A;

heavy metals including, but not limited to, arsenic, cadmium, lead, and mercury;

terpenes including, but not limited to, (1) monoterpenes such as camphene, camphor, 3-carene, α-cedrene, cedrol, endo-fenchyl alcohol, eucalyptol, fenchone, geraniol, geranul acetate, hexahydrothymol, isoborneol, isopulegol, limonene, linalool, p-mentha-1,5-diene, β-myrcene, α- and β-pinene, pulegone, sabinene and hydrate, α- and γ-terpinene, terpineol, terpinolene, α-, β-, and γ-terpineol, nerol, borneol, and ocimene isomers I and II, and (2) sesquiterpenes such as α-bisabolol, β-caryophyllene, caryophyllene oxide, guaiol, α-humulene, cis- and trans-nerolidol, and valencene; as well as mixtures thereof.

In some embodiments, the rapidly infusing composition is formulated with a form of CBD which contains less than 1 wt. %, preferably less than 0.5 wt. %, preferably less than 0.1 wt. %, preferably less than 0.05 wt. %, preferably less than 0.001 wt. %, preferably 0 wt. % of the above listed impurities, based on a total weight of the CBD material, with specific mention being made to THC. In some embodiments, the rapidly infusing composition is formulated with a form of CBD which contains no impurity, such as those listed above, in an amount above the limits of detection (LOD) and/or limits of quantification (LOQ) for the technique/instrumentation being used to make such a determination. For example, preferred rapidly infusing compositions are those formulated with a pure form of CBD which has a THC content of less than 0.1577 wt. %, preferably less than 0.1 wt. %, preferably less than 0.01 wt. %, preferably less than 0.001 wt. %, based on a total weight of the CBD material. In preferred embodiments, the rapidly infusing composition is formulated with a pure form of CBD which consists of, or consists essentially of, CBD.

The full effects of the present disclosure may not be realized when the rapidly infusing composition is formulated with an impure form of CBD or when the composition is formulated with CBD in oil/liquid form. Without being bound by theory, it is believed that during the manufacture of the rapidly infusing composition, when the CBD is in solid form with sufficiently high purity, lyophilization from a drug product suspension generates a structured and robust matrix of gelatin as the water is removed via sublimation, and an even distribution of the CBD throughout the gelatin matrix. Such a structured assembly of CBD suspended within a gelatin matrix is believed to afford the rapidly infusing composition with rapid disintegration properties and efficient transfer of CBD from the hydrophilic vehicle to the mucous membrane of the buccal cavity, or the ventral surface under the tongue, upon administration.

On the contrary, when the composition is formulated with an impure (oil) form of CBD during manufacture, lyophilization is instead performed from an o/w emulsion of CBD, which may produce an unstable, disordered matrix of gelatin more prone to collapse back into an oil or semi-solid state. The resulting composition tends to suffer from poor shelf-life, increased disintegration times, and inferior delivery/uptake of the CBD into systemic circulation reflected in longer onset times and overall less efficacy against pain indications.

Accordingly, any CBD manufacturing method known by those of ordinary skill in the art which provides CBD in solid form, and of sufficient purity, may be utilized herein for preparation of the CBD ATI. For illustration purposes, one exemplary CBD manufacturing method is described below, although it should be understood that numerous modifications and variations are possible, and the CBD may be produced using methods or techniques otherwise than as specifically described.

CBD may be extracted/isolated from biomass, for example, a cured flower of *Cannabis sativa* L. The biomass may contain, for example, at least 1 mg/g, preferably at least 2 mg/g, preferably at least 3 mg/g, and up to 10 mg/g, preferably up to 8 mg/g, preferably up to 6 mg/g, preferably up to 4 mg/g of CBD; at least 50 mg/g, preferably at least 60 mg/g, preferably at least 70 mg/g, preferably at least 80 mg/g, preferably at least 90 mg/g, and up to 150 mg/g, preferably up to 140 mg/g, preferably up to 130 mg/g, preferably up to 120 mg/g, preferably up to 110 mg/g, preferably up to 100 mg/g of cannabidiolic acid (CBDa); and no detectable amount of THC. Extraction of the biomass with an alcoholic solvent (e.g., ethanol) and cooling may form a tincture. The tincture may be filtered to remove sediment and particulates, and concentrated, for example, using a rotary evaporator.

An aluminum phyllosilicate clay (e.g., bentonite) may then be mixed with the concentrated product at a weight ratio of at least 2:1, preferably at least 3:1, preferably at least 4:1, and up to 6:1, preferably up to 5:1, and the resulting mix filtered to remove fats, waxes, and lipids. The product may then be frozen/winterized, after which the frozen product may be again filtered and taken through another solvent removal/recovery cycle to form a winterized crude.

Decarboxylation of the winterized crude by heating, for example in an induction oven centrifugal reactor, may be performed to remove the carboxylic acid functionality from the cannabinoids. Distillation of the decarboxylated material may then provide a distillate.

The distillate may then be precipitated in a high-pressure reactor using an alkane solvent (e.g., pentane), and a cryo-chamber may be used to subject the precipitate to cryo temperatures (e.g., −20° F. to −40° F.) to promote the growth of crystalline CBD. The CBD crystals may be washed with an alkane solvent (e.g., pentane), filtered, and ground to a finer particle size, prior to being purged in a vacuum oven for removal of solvents and impurities. The obtained solid CBD may then be analyzed for purity, as appropriate.

Methods to be used for preparing the rapidly infusing composition are preferably pharmaceutical-GMP compliant, and may include generally bringing into association the ATI (e.g., CBD) with the gelatin and sugar alcohol (e.g., mannitol), and, optionally, one or more accessory pharmaceutically acceptable carrier and/or excipient ingredients, in water to form a drug product suspension which is then lyophilized.

One exemplary method for manufacturing the rapidly infusing composition is presented below (and depicted in the FIGURE), although it should be understood that numerous modifications and variations are possible, and the rapidly infusing composition may be produced using methods or techniques otherwise than as specifically described.

Purified water, gelatin, and sugar alcohol (e.g., mannitol) may be charged to a mixer, for example a pot equipped with an overhead stirrer, and heated (e.g., 40 to 80° C.) with agitation until complete solvation. Any desired sweetener (e.g., a mixture of sucralose and acesulfame-K) may then be added and allowed to dissolve.

Upon cooling, for example to 20 to 35° C., the solution may next be transferred to a homogenizer, and the ATI (e.g., CBD) may be subsequently charged and dispersed using the homogenizer, with preferable micronization of the ATI, to form a drug product suspension. Any desired flavorant and colorant may be added at this point with continued mixing. The drug product suspension may be transferred to a second mixer whilst maintaining a cooled temperature (e.g., 20 to 35° C.).

In a blistering machine equipped with a dosing system, blister pockets may next be filled with the drug product suspension until achieving a target dose weight, followed by freezing in a suitable cryochamber. The blister trays may be transferred from the cryochamber to a suitable refrigerated storage cabinet (e.g., at a temperature below 0° C.) to keep the product frozen prior to lyophilization. Then, the frozen blisters may be loaded into a lyophilizer and subject to lyophilization to sublimate the water and form the rapidly infusing compositions. Finally, when the lyophilization cycle is deemed complete, final sealing (e.g., heat sealing of blister lidding) may be performed to provide the rapidly infusing compositions in single dose units in individual blister units.

In preferred embodiments, the rapidly infusing composition comprises, consists essentially of, or consists of gelatin, mannitol, sweetener, flavorant, colorant, and as the ATI, CBD.

Also contemplated for use as an active therapeutic ingredient are derivatives/analogs of CBD that retain the desired activity for the treatment of pain. Derivatives/analogs that retain substantially the same activity as CBD, or more preferably exhibit improved activity, may be produced according to standard principles of medicinal chemistry, which are well known in the art. Such derivatives/analogs may exhibit a lesser degree of activity than CBD, so long as they retain sufficient activity to be therapeutically effective. Derivatives/analogs may exhibit improvements in other properties that are desirable in active therapeutic agents such as, for example, improved solubility, reduced toxicity, enhanced uptake, increased bioavailability, etc. Contemplated CBD derivatives/analogs include, but are not limited to, cannabidiolic acid compounds and variants thereof, such as cannabidiolic acid and esters of cannabidiolic acid, in particular alkyl esters of cannabidiolic acid (e.g., cannabidiolic acid methyl ester); 5' side chain modified CBD compounds such as cannabidivarin (CBDV), cannabidiol-dimethylheptyl (CBD-DMH), and 1,2-cannabidiol-dimethylheptyl (1,2-CBD-DMH); 7-methyl modified CBD compounds such as 7-carboxy cannabidiol (7-COOH-CBD) and 7-hydroxy cannabidiol (7-OH-CBD); hydrogenated CBD compounds such as 8,9-dihydrocannabidiol ($H_2$-CBD) and tetrahydrocannabidiol ($H_4$-CBD); halogenated CBD compounds such as 3'-chloro-CBD, 3',5'-dichloro-CBD, 3'-bromo-CBD, 3',5'-dibromo-CBD, 3'-iodo-CBD, and 3',5'-diiodo-CBD; hydroxyl group modified CBD compounds such as desoxy-CBD and dimethylether CBD; cannabielsoin (CBE); machaeridiols A, B, and C; as well as any pharmaceutically acceptable salts, solvates, and/or stereoisomers of such compounds. When a CBD derivative/analog is used as the ATI in the disclosed rapidly infusing composition, particular preference is given to cannabidiolic acid methyl ester.

It is contemplated that CBD or derivatives/analogs of CBD may be useful in combination. It is also contemplated that CBD or derivatives/analogs of CBD may be useful in combination with current Standards of Care for the treatment of pain as well as any that evolve over the foreseeable future. Specific dosages and dosing regimens would be based on physicians' evolving knowledge and the general skill in the art.

Therapeutic Applications and Methods

The present disclosure provides a method of treating pain in a subject. The method involves administering to the subject in need thereof the disclosed rapidly infusing composition, in one or more of its embodiments, as a therapeutic agent for the treatment of pain. The methods herein may be used to manage pain/induce an analgesic response prior to, during, or following treatment of a disease, condition, or pathology. Both palliative and curative treatment methods are contemplated herein. Additionally, treatment may be performed on a susceptible subject in order to prevent or minimize a condition or other adverse physiological event or on a clinically symptomatic subject in order to achieve one or more of the desired treatment effects (e.g., reducing pain symptoms). In preferred embodiments, the subject is a human.

The methods of the present disclosure may be used to treat any type of pain. The pain may be categorized as nociceptive pain, neuropathic pain, or psychogenic pain. This includes subsets thereof including, but not limited to, phantom pain, breakthrough pain, incident pain, inflammatory pain, post-surgical (postoperative) pain, cancer-associated pain, peripheral pain, central pain, and spastic pain. The types of pain that may be treated with the methods herein may be acute pain types, or may be considered chronic pain types.

In preferred embodiments, the methods of the present disclosure may be used to treat neuropathic pain. The neuropathic pain may be central neuropathic pain, peripheral neuropathic pain, or both. The neuropathic pain may also be categorized as acute neuropathic pain or chronic neuropathic pain. Examples of categories of neuropathic pain that may be treated by the methods of the present disclosure include, but are not limited to, autonomic neuropathy; focal neuropathy; proximal neuropathy; diabetic neuropathy; compression neuropathy; phantom limb pain; neuralgia (e.g., trigeminal neuralgia, postherpetic neuralgia); thoracic or lumbar radiculopathy; complex regional pain syndromes; neuropathic pain associated with AIDS and infection with the human immunodeficiency virus; cancer-associated pain such as neuropathic cancer pain (NCP) attributable to the cancer per se and/or the various cancer treatments (e.g., chemotherapy, radiotherapy, and surgery) that a subject with cancer may endure; and peripheral neuropathies such as drug-induced neuropathy and postsurgical (postoperative) neuropathy.

Thus, in some embodiments, the present disclosure provides a method of treating pain in a subject who has a disease or condition which causes neuropathic pain. Examples of such diseases or conditions include, but are not limited to, an abdominal wall defect, an abdominal migraine, achondrogenesis, acquired immunodeficiency syndrome (AIDS), porphyria (e.g., acute porphyrias), acute brachial neuritis, acute toxic epidermolysis, adiposa dolorosa, adrenal neoplasm, adrenomyeloneuropathy, adult or childhood dermatomyositis, amyotrophic lateral sclerosis, arachnoiditis, arteritis giant cell and cranial arteritis, arthritis, astrocytoma athetoid cerebral palsy, tumors of the central nervous system, brachial neuritis, brachiocephalic ischemia, brain tumors, Burkitt's lymphoma, neurofibromatosis, cervical spinal stenosis, Charcot-Marie-Tooth disease, chronic inflammatory demyelinating polyneuropathy, complex regional pain syndrome, congenital dysmyelinating neuropathy, tethered (spinal) cord syndrome, demyelinating disease, diabetes mellitus, disseminated sclerosis, Ehlers-Danlos syndrome, endometriosis, fibromyalgia, fibromyositis, fibrositis, Guillain-Barre syndrome, hereditary sensory and autonomic neuropathy, Hodgkin's disease (lymphoma), hypertrophic interstitial neuropathy, idiopathic cervical dystonia, lumbar spinal stenosis, lupus, mononeuritis (multiplex, peripheral, etc.), multiple myeloma, multiple osteochondromatosis, multiple sclerosis, musculoskeletal pain syndrome, neuropathic amyloidosis, neuropathic beriberi, brachial plexus neuropathy, Niemann-Pick disease, osteoarthritis, osteogenesis imperfecta, peripheral neuritis, polymyositis, postherpetic neuralgia, radial nerve palsy, radicular neuropathy, sickle cell disease, spina bifida, spinal arteriovenous malformation, Still's disease, syringomyelia, systemic sclerosis, and thalamic pain syndrome.

In some embodiments, the present disclosure provides a method of treating postsurgical (postoperative) pain in a subject who has undergone a surgical procedure by administering the rapidly infusing composition post-operatively to the subject. Postsurgical pain is a type of pain that usually differs in quality and location from pain experienced prior to surgery, and is usually associated with iatrogenic neuropathic pain caused by surgical injury to a major peripheral nerve (surgically-induced neuropathic pain or SNPP). The postsurgical pain may be acute, or if the pain state persists well after the surgical procedure, for example, more than 2 months after surgery, then the postsurgical pain may be of the chronic variety.

A wide variety of surgical procedures may cause postsurgical pain, and the methods disclosed herein may be used for treating pain stemming from any surgical procedure including, but not limited to, those involving excision of an organ (-ectomy), those involving cutting into an organ or tissue (-otomy), those involving minimally invasive procedures like making a small incision and insertion of an endoscope (-oscopy), those involving formation of a permanent or semi-permanent stoma in the body (-ostomy), those involving reconstruction or cosmetic procedures (-oplasty), those involving repair of damaged or congenital abnormal structure (-rraphy), reoperation procedures, amputations, and resections, including those surgical procedures of the manual or robot-assisted varieties.

Types of surgical procedures may include, but are not limited to bariatric surgery, breast surgery, colon and rectal surgery, endocrine surgery, surgeries which fall under the general surgery classification, gynecological surgery, head and neck surgery, hernia surgery, neurosurgery, orthopedic surgery, ophthalmological surgery, oral or maxillofacial surgery, surgeries which fall under the outpatient surgery classification, thoracic surgery, urologic surgery, and vascular surgery. Specific mention is made herein to inguinal hernia repair, amputation (e.g., leg amputation), caesarean section, coronary artery bypass surgery, gastric bypass surgery, hand surgery, Achilles tear surgery, open-knee surgery, spinal surgery, arthroscopy of the knee, shoulder, hip, ankle, elbow, or wrist, and arthroplasty of the knee, shoulder, hip, ankle, elbow, or wrist. The methods disclosed herein may be particularly well-suited for the treatment of postsurgical pain associated with orthopedic procedures including, but not limited to, knee arthroplasty (knee replacement surgery) and shoulder arthroscopy. The disclosed methods may also be particularly well-suited for treating postsurgical pain in subjects whom have not responded well to opioids or whom have experienced one or more significant opioid-related side effects such as addiction, cognitive impairment, constipation, nausea, and myoclonus.

In some embodiments, the present disclosure provides a method of treating cancer-associated pain in a subject who has cancer. Cancer-associated pain may be caused by the cancer itself, i.e., from the cancer growing into/destroying nearby tissue, nerves, bones, organs, etc. The cancer-associated pain may be caused by the chemicals released by certain tumor types, or the subject's response (e.g., immunoresponse) to the released chemicals. The cancer-associated pain may also be caused by various types of cancer treatment that the subject may undergo after diagnosis, such as surgery, radiation therapy, and therapy with agents having cytostatic or antineoplastic activity (e.g., chemotherapy). Cancer-associated pain stemming from any/all of the above causes may be treated with the methods disclosed herein.

In general, the subject may have any cancer that fails to undergo apoptosis, including both solid tumor types (e.g., carcinomas, sarcomas including Kaposi's sarcoma, erythroblastoma, glioblastoma, meningioma, astrocytoma, melanoma, myoblastoma, and the like) and non-solid tumor cancers such as leukemia. Types of cancers which can cause cancer-associated pain treatable by the disclosed methods include, but are not limited to, brain cancers, skin cancers, bladder cancers, ovarian cancers, breast cancers, gastric cancers, pancreatic cancers, prostate cancers, colon/colorectal cancers, blood cancers, lung cancers, and bone cancers, including a combination of two or more cancer types. Examples of such cancer types include, but are not limited to, neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma, plasmocytoma, and adrenal tumors.

The methods of the present disclosure may be particularly advantageous for treating cancer-associated pain in subjects having advanced stage cancer, or who are otherwise in a chronic progressive cancer-associated pain state, with particular mention being made to those subjects having pancreatic cancer, and especially advanced pancreatic cancer, and are experiencing pancreatic cancer-associated pain. The disclosed methods may also be particularly well-suited for treating cancer-associated pain in subjects whom have not responded well to opioids or whom have experienced one or more significant opioid-related side effects such as addiction, cognitive impairment, constipation, nausea, and myoclonus.

The rapidly infusing composition of the present disclosure may be administered to subjects who have not received cancer treatment, who are undergoing cancer treatment (i.e., the rapidly infusing composition is co-administered with a cancer treatment), or who have previously completed one or more rounds of cancer treatment. Examples of cancer treatments include, but are not limited to, surgery, radiation therapy, and therapy with one or more agents having cytostatic or antineoplastic activity.

Agents having cytostatic or antineoplastic activity may generally fall into the following categories: (i) antimetabolites; (ii) DNA-fragmenting agents; (iii) DNA-crosslinking agents; (iv) intercalating agents; (v) protein synthesis inhibitors; (vi) topoisomerase I poisons; (vii) topoisomerase II poisons; (viii) microtubule-directed agents; (ix) kinase inhibitors; (x) miscellaneous investigational agents; (xi) hormones; (xii) hormone antagonists; (xiii) antiangiogenic agents; and (xiv) targeted therapies; with specific mention being made to mitotic/tubulin inhibitors, alkylating agents, cell cycle inhibitors, enzymes, topoisomerase inhibitors, biological response modifiers, anti-hormones, tyrosine-kinase inhibitors, inhibitors of MMP-2, MMP-9, or COX-2, antiandrogens, platinum coordination complexes, adrenocortical suppressants, progestins, antiestrogens, androgens, aromatase inhibitors, thymidylate synthase inhibitors, thymidine phosphorylase (TPase) inhibitors, and DNA synthesis inhibitors. Specific examples of which include, but are not limited to, paclitaxel, epothilone, docetaxel, discodermolide, etoposide, vinblastine, vincristine, teniposide, vinorelbine, vindesine, imatinib, nilotinib, dasatinib, bosutinib, ponatinib, bafetinib, busulfan, carmustine, chlorambucil, cyclophosphamide, cyclophosphamide, dacarbazine, ifosfamide, lomustine, mechlorethamine, melphalan, mercaptopurine, procarbazine, cladribine, cytarabine, fludarabine, gemcitabine, pentostatin, 5-fluorouracil, clofarabine, capecitabine, methotrexate, thioguanine, daunorubicin, doxorubicin, idarubicin, mitomycin, actinomycin, epirubicin, irinotecan, mitoxantrone, topotecan, camptothecin, tipiracil, trifluridine, oxaliplatin, bicalutamide, tamoxifen, anastrozole, exemestane, testosterone propionate, cetuximab, bevacizumab, panitumumab, zivaflibercept, ramucirumab, and mixtures thereof.

The methods of treating cancer pain described herein also provide a unique opportunity to clinically determine the potential direct beneficial impact of CBD, or other cannabinoids, or derivative/analogs of CBD or other cannabinoids, on cancer itself. For example, CBD agents have been shown to reduce growth and metastases in mouse models of pancreatic cancer (Carracedo A, Gironella M, Lorente M, et al. Cannabinoids induce apoptosis of pancreatic tumor cells via endoplasmic reticulum stress-related genes. Cancer Res 2006; 66:6748-55). The preferred embodiments described herein, including the use of rapidly infusing composition, preferably with an oral disintegration time of 1-5 seconds, provides for the first time the opportunity to clinically test these potential benefits in humans by increasing patient compliance and providing superior control of effective CBD agent dosing to any prior known method.

In some embodiments, the present disclosure provides a method of treating inflammatory pain in a subject who is experiencing acute or chronic pain that results from inflammatory processes, such as may arise in the case of infections, arthritis, tissue damage, and neoplasia or tumor related hypertrophy. Cancer-associated pain may, therefore, in certain circumstances, be considered to fall within the category of inflammatory pain. Other examples of inflammatory diseases or conditions which can cause inflammatory pain include, but are not limited to, arthritis (e.g., osteoarthritis, rheumatoid arthritis, etc.), lupus, aspiration pneumonia, empyema, gastroenteritis, necrotizing pneumonia, pelvic inflammatory disease, pharyngitis, pleurisy, urinary tract infections, and chronic inflammatory demyelinating polyneuropathy. In addition to treating the pain symptoms associated with the inflammatory disease or condition, the methods described herein may be particularly beneficial in the treatment of inflammatory pain varieties when the rapidly infusing composition is formulated with an ATI which also reduces the inflammation condition at the root of the pain state, as may be the case when the rapidly infusing composition is formulated with CBD or a derivative/analog thereof.

The method of the present disclosure may also be applied for the treatment of pain associated with muscle spasticity. Muscle spasticity is a relatively common problem among subjects suffering from central neurologic problems, such as cerebrovascular pathology, medullar injuries, multiple sclerosis, and cerebral palsy, as well as subjects suffering from adductor muscle spasms associated with hemiplegia or paraplegia.

With respect to administration, the rapidly infusing composition is preferably administered to the subject via one or more of the oral mucosae, preferably via the buccal mucosa (buccally) or the sublingual mucosa (sublingually). Advantages of oral mucosal delivery include the ease of administration, the ability to bypass first pass metabolic processes thereby enabling higher bioavailability than through enteral delivery via the gastrointestinal tract, less variability between patients, sustained drug delivery, and extensive drug absorption and rapid onset of therapeutic action due to either a large surface area in the case of sublingual administration or high-levels of vascularization in the case of buccal administration. Administration may be carried out by simply placing the rapidly infusing composition directly in the buccal cavity (between the cheek and gum) or over the sublingual mucous gland (under the ventral surface of the tongue). While the sublingual mucosa has a large surface area and extremely good permeability, the blood supply (blood flow) is lesser than that of the buccal cavity. Furthermore, sublingual administration tends to stimulate the flow of saliva more than buccal administration, and the increased saliva production may make it more difficult for patients to avoid swallowing. Any amount of ATI that is swallowed would be subject to first pass metabolism and thus overall lower bioavailability. Swallowing further results in greater variability in the effective amount of dosing, as a result of, including but not limited to, the variability in the amount swallowed and the greater patient variability of bioavailability through first-pass metabolism for the amount swallowed. Therefore, in preferred embodiments, the rapidly infusing composition is administered buccally (through the buccal mucosa). The rapid disintegration of the rapidly infusing composition, approximately in 1-5 seconds in preferred embodiments, and buccal administration together combine to provide optimal dosing control by limiting the time for potential swallowing and ensuring that the vast majority of the ATI is absorbed through the buccal mucosa. Administration may be performed by the subject (self-administered) or by someone other than the subject, for example, a healthcare provider, family member, etc.

The actual amount of ATI administered to the subject may be varied so as to achieve the desired therapeutic response for a particular subject, composition, and mode of administration, without being toxic to the subject. The selected amount of ATI administered to the subject will depend upon a variety of factors including the activity of the ATI employed, the route of administration, the time of administration, the rate of excretion or metabolism of the particular compound being employed, the rate and extent of absorption, the duration of the treatment, other drugs, compounds, and/or materials used in combination with the rapidly infusing composition, the age, sex, weight, condition, general health, and prior medical history of the subject being treated, and like factors well known in the medical arts.

A physician having ordinary skill in the art can readily determine and prescribe the effective amount of the ATI required. For example, the physician could start doses of the ATI at levels lower than that required in order to achieve the desired therapeutic effect and gradually increase the dosage until the desired effect is achieved. In general, a suitable dose of the ATI will be that amount which is the lowest dose effective to produce a therapeutic effect, which will generally depend upon the factors described above. Typically, when the ATI is CBD or a derivative/analog thereof, the therapeutically effective amount of CBD or a derivative/analog thereof will range from at least 10 mg, preferably at least 15 mg, preferably at least 20 mg, preferably at least 25 mg, preferably at least 30 mg, preferably at least 35 mg, preferably at least 40 mg, preferably at least 45 mg, preferably at least 50 mg, and up to 100 mg, preferably up to 95 mg, preferably up to 90 mg, preferably up to 85 mg, preferably up to 80 mg, preferably up to 75 mg, preferably up to 70 mg, preferably up to 65 mg, preferably up to 60 mg, preferably up to 55 mg of CBD or derivative/analog thereof per dose. In preferred embodiments, the rapidly infusing composition is administered to the subject to provide 25 to 50 mg of CBD or derivative/analog thereof per dose (dosing event).

Relative to subject body weight, the therapeutically effective amount of CBD or derivative/analog thereof administered to the subject per dose will typically range from at least 0.1 mg/kg, preferably at least 0.15 mg/kg, preferably at least 0.2 mg/kg, preferably at least 0.25 mg/kg, preferably at least 0.3 mg/kg, preferably at least 0.35 mg/kg, preferably at least 0.4 mg/kg, preferably at least 0.45 mg/kg, preferably at least 0.5 mg/kg, preferably at least 0.55 mg/kg, preferably at least 0.6 mg/kg, and up to 5 mg/kg, preferably up to 4 mg/kg, preferably up to 3 mg/kg, preferably up to 2 mg/kg, preferably up to 1 mg/kg, preferably up to 0.95 mg/kg, preferably up to 0.9 mg/kg, preferably up to 0.85 mg/kg, preferably up to 0.8 mg/kg, preferably up to 0.75 mg/kg, preferably up to 0.7 mg/kg, preferably up to 0.65 mg/kg.

In order to achieve the above described therapeutically effective amount per dose, the methods herein may involve administering one, or more than one, unit of the rapidly infusing composition per dose (dosing event). For example, in circumstances where each unit of the rapidly infusing composition contains 25 mg of ATI (e.g., CBD), and it has been determined that the subject requires a therapeutically effective amount of 50 mg of ATI per dose, then the subject may be given two (2) units (e.g., tablets) to achieve the desired therapeutically effective amount of 50 mg ATI per dose. Accordingly, depending on the unit dose of ATI in each unit of the rapidly infusing composition, the therapeutically effective amount of ATI prescribed, etc., 1, 2, 3, 4, 5, or more units (e.g., tablets) may be administered to the subject per dose. Accordingly, the phrases "administering to the subject in need thereof a rapidly infusing composition", "the rapidly infusing composition is administered", etc., are intended herein to include administration of a single unit (e.g., tablet), or multiple units (e.g., tablets), to the subject in order to provide the therapeutically effective amount of ATI, e.g., CBD. While it may be possible to administer partial (e.g., half) tablets to the subject, for practical reasons, it is preferred that one or more whole tablets are administered to the subject.

In many instances, the dose schedule (frequency of administration) may be determined simply on the basis of when the subject requires pain relief. Thus in some embodiments, the rapidly infusing composition may be administered 'as needed' (PRN). In other embodiments, the subject may be prescribed a dosage regimen that involves multiple, separate dosing events at appropriate time intervals throughout the day. In any case, the subject may be administered a therapeutically effective amount of ATI 1 time, 2 times, 3 times, 4 times, 5 times, 6 times, 7 times, 8 times, 9 times, 10 times, or even more times, optionally at appropriate intervals, throughout the day. A particularly preferred dosing schedule involves administration of the rapidly infusing composition 3 times per day (t.i.d.). The rapidly infusing composition may also be administered on an hourly dosing schedule (q), for example, administration may take place every 1, 2, 3, 4, 5, 6, 7, 8, 9, 10, 11, 12, 13, 14, 15, 16, 17, 18, 19, 20, 21, 22, 23 or 24 hours, as appropriate. When the ATI is CBD or a derivative/analog thereof, the maximum daily dosage of CBD or derivative/analog thereof is preferably no more than 1,000 mg, preferably no more than 900 mg, preferably no more than 800 mg, preferably no more than 700 mg, preferably no more than 600 mg, preferably no more than 500 mg, preferably no more than 400 mg, preferably no more than 300 mg, preferably no more than 200 mg, preferably no more than 150 mg, preferably no more than 100 mg, preferably no more than 75 mg CBD or derivative/analog thereof, per day.

Treatment may involve administration on consecutive days, or otherwise, until satisfactory pain relief is achieved. For example, the subject may be administered a therapeutically effective dose, at least 1 time per day and up to 10 times per day, for 1 day, 2 days, 3 days, 4 days, 5 days, 6 days, 7 days, 8 days, 9 days, 10 days, 11 days, 12 days, 13 days, 14 days, or more, such as weeks, months, or even years, until the pain state has been sufficiently treated.

Preferred dosing regimens are those involving a consistent dosing amount and schedule. One non-limiting example of a dosing regimen may involve the subject taking one unit of the rapidly infusing composition (e.g., 25 mg CBD)—therapeutically effective amount of 25 mg CBD per dose—three times per day (t.i.d.), for 14 consecutive days. Another non-limiting example of a dosing regimen may involve the subject taking two units of the rapidly infusing composition (e.g., 25 mg CBD each) therapeutically effective amount of 50 mg CBD per dose—three times per day (t.i.d.), for 10 consecutive days.

Upon being administered buccally (between the cheek and gum) or sublingually (under the ventral surface of the tongue), the rapidly infusing composition preferably disintegrates in 5 seconds or less, preferably 4 seconds or less, preferably 3 seconds or less, preferably 2 seconds or less, preferably 1 second or less. Further, this route of administration may provide a single dose bioavailability of at least 50%, preferably at least 55%, preferably at least 60%, preferably at least 65%, preferably at least 70%, preferably at least 75%, preferably at least 80%, preferably at least 85%, preferably at least 90%, and up to 99%, preferably up to 98%, preferably up to 96%, preferably up to 95%, preferably up to 92%.

Besides efficacy of treatment and general relief from pain symptoms, pharmacokinetic outcomes may provide another useful measure of in vivo performance. In this regard, the rapidly infusing composition formulated with CBD and administered according to the methods described herein may provide a time to maximum plasma concentration (Tmax) of less than 5 hours, preferably less than 4 hours, preferably less than 3 hours, preferably less than 2 hours, preferably less than 1 hour, preferably less than 45 minutes, preferably less than 30 minutes, preferably less than 15 minutes; an area under the plasma concentration versus time curve (AUC) of at least 1 h×ng/mL, preferably at least 3 h×ng/mL, preferably at least 5 h×ng/mL, preferably at least 10 h×ng/mL, preferably at least 15 h×ng/mL, preferably at least 20 h×ng/mL, preferably at least 25 h×ng/mL, preferably at least 30 h×ng/mL, and up to 80 h×ng/mL, preferably up to 70 h×ng/mL, preferably up to 60 h×ng/mL, preferably up to 50 h×ng/mL, preferably up to 40 h×ng/mL, from a single (1) unit of rapidly infusing composition formulated with 25 mg CBD; and a mean plasma half-life ($t_{1/2}$) of CBD of at least 1 hour, preferably at least 2 hours, preferably at least 3 hours, preferably at least 4 hours, preferably at least 5 hours, preferably at least 6 hours, and up to 12 hours, preferably up to 11 hours, preferably up to 10 hours, preferably up to 9 hours, preferably up to 8 hours, preferably up to 7 hours, for a single dose, but may provide a significantly higher mean plasma half-life ($t_{1/2}$) after prolonged buccal or sublingual administration (e.g., $t_{1/2}$ of 2 to 5 days).

Using the platform, the rapidly infusing composition may be used as a stand-alone therapeutic agent for pain relief or may be used in combination therapy—wherein the rapidly infusing composition is used in combination with one or more other forms of therapy such as one or more second therapeutic agents. The combination therapy may be applied to treat pain or a combination of pain and a different condition such as cancer.

Combination therapy may involve administering the rapidly infusing composition formulated with e.g., CBD or a derivative/analog thereof, in combination with one or more second therapeutic agents that provides an analgesic effect for the treatment of pain. For example, rapidly infusing compositions formulated with CBD or a derivative/analog thereof may be used as an adjunct to traditional analgesics such as opioid analgesics and non-steroidal anti-inflammatory drugs (NSAIDs) or other Standard of Care for pain management such as antidepressants or anticonvulsants.

In particular, rapidly infusing compositions formulated with CBD or a derivative/analog thereof may advantageously function as an opioid-sparing medication, that when co-administered with opioids, enables a reduced opioid dose or shorter opioid dosage period, without a loss of analgesic efficacy. Opioids suitable for use in combination therapy may include natural opiates, esters/ethers of morphine opiates, semi-synthetic opioids, synthetic opioids, and endogenous opioid peptides, examples of which include, but are not limited to, morphine, codeine, thebaine, oripavine, papaveretum, diacetylmorphine, nicomorphine, dipropanoylmorphine, diacetyldihydromorphine, acetylpropionylmorphine, desomorphine, methyl desomorphine, dibenzoylmorphine, dihydrocodeine, ethylmorphine, heterocodeine, buprenorphine, etorphine, hydrocodone, hydromorphone, oxycodone, oxymorphone, fentanyl, alphamethylfentanyl, alfentanil, sufentanil, remifentanil, carfentanyl, ohmefentanyl, pethidine, ketobemidone, desmethylprodine, allylprodine, prodine, phenethyl phenyl acetoxypiperidine, promedol, propoxyphene, dextropropoxyphene, dextromoramide, bezitramide, piritramide, methadone, dipipanone, levomethadyl acetate, difenoxin, diphenoxylate, loperamide, dezocine, pentazocine, phenazocine, dihydroetorphine, butorphanol, nalbuphine, levorphanol, levomethorphan, racemethorphan, lefetamine, meptazinol, mitragynine, tilidine, tramadol, tapentadol, eluxadoline, AP-237, and 7-hydroxymitragynine.

NSAIDs suitable for use in combination therapy may include, but are not limited to, oxicams, salicylates, acetic acid derivatives, fenamates, propionic acid derivatives, pyrazoles/pyrazolones, coxibs, and sulfonanilides, with specific mention being made to piroxicam, isoxicam, tenoxicam, sudoxicam, salicylic acid, ethyl salicylate, methyl salycilate, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, mefenamic, meclofenamic, flufenamic, niflumic, tolfenamic acids, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, trimethazone, ramifenazone, lonazolac, meloxicam, celecoxib, and the like. Other analgesics without anti-inflammatory activity such as paracetamol (acetaminophen) may also be used.

Antidepressants suitable for use in combination therapy may include, but are not limited to, tricyclic antidepressants such as amitriptyline, doxepin, imipramine, desipramine, and nortriptyline; selective serotonin reuptake inhibitors such as paroxetine and citalopram; venlafaxine; bupropion; and duloxetine.

Anticonvulsants suitable for use in combination therapy may include, but are not limited to, voltage-gated ion channel blockers, ligand-gated ion channel blockers, antagonists of the excitatory receptors for glutamate and N-methyl-D-aspartate, and enhancers of the γ-aminobutyric acid, with specific mention being made to, carbamazepine, gabapentin, lamotrigine, pregabalin, baclofen, phenytoin, and the like.

Combination therapy may involve administering the rapidly infusing composition formulated with e.g., CBD or a derivative/analog thereof, in combination with two or more second therapeutic agents that provides an analgesic effect, with specific mention being made to oxycodone/paracetamol, propoxyphene/paracetamol, codeine/paracetamol, hydrocodone/paracetamol, and the like.

The rapidly infusing composition may also be used in conjunction with one or more regional nerve blockades (nerve block), as appropriate, including, but not limited to, a brachial plexus block such as an intrascalene block, an occipital nerve block, an intercostal nerve block, a sciatic nerve block, a spinal block, an intraarticular block, and an adductor canal peripheral nerve block.

Combination therapy may also involve administering the rapidly infusing composition formulated with e.g., CBD or a derivative/analog thereof, in combination with one or more second forms of therapy for the treatment of a condition other than pain, for example, one or more cancer therapies. Examples of cancer therapies include, but are not limited to, surgery, radiation therapy, and therapy with agents having cytostatic or antineoplastic activity, such as those described previously. Thus, in some embodiments, the methods of the present disclosure involve co-administration of the rapidly infusing composition (for pain relief) and a cancer treatment such as radiation therapy and/or an agent with cytostatic or antineoplastic activity (for cancer treatment), including any of those agents with cytostatic or antineoplastic activity falling into the 14 classes described above, as well as any future agents that may be developed.

Combination therapy is intended to embrace administration of these therapies in a sequential manner, that is, wherein the rapidly infusing composition and one or more other therapies are administered at a different time, as well as administration of these therapies, or at least two of the therapies, in a substantially simultaneous manner. Substantially simultaneous administration can be accomplished, for example, by administering to the subject multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, the rapidly infusing composition formulated with CBD or a derivative/analog thereof may be administered via buccal administration while a second therapeutic agent of the combination may be administered intravenously. Alternatively, for example, all therapeutic agents may be administered buccally. Combination therapy also can embrace the administration of the rapidly infusing composition in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agent(s) and non-drug treatment is achieved. For example, in appropriate cases, the beneficial effect is still achieved when the non-drug treatment is temporally removed from the administration of the therapeutic agents, perhaps by days or even weeks.

The examples below are intended to further illustrate the materials and methods of the present disclosure, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

The present disclosure also contemplates other embodiments "comprising", "consisting of" and "consisting essentially of", the embodiments or elements presented herein, whether explicitly set forth or not.

All patents and other references mentioned above are incorporated in full herein by this reference, the same as if set forth at length.

Obviously, numerous modifications and variations of the present invention are possible in light of the above teachings. It is therefore to be understood that, within the scope of the appended claims, the invention may be practiced otherwise than as specifically described herein.

Examples

Rapidly Infusing Composition

Ingredients

The ingredients that were used to make the rapidly infusing composition and the placebo are given in Table 1. USP=United States Pharmacopeia. EP=European Pharmacopoeia. NF=National Formulary.

TABLE 1

| Ingredients | | |
|---|---|---|
| Ingredient | Primary Function | Specification |
| Gelatin | Matrix former | USP/EP/NF |
| Mannitol | Bulking agent | USP/EP |
| Lemon-lime flavor powder | Flavorant | Non-compendial |
| CBD isolate | ATI | Non-compendial |
| Sucralose | Sweetener | USP/NF |
| Acesulfame-K | Sweetener | USP/NF |
| FD&C Yellow #5 | Colorant | Non-compendial |
| Purified water | Vehicle | USP/EP |

An example rapidly infusing composition was made using the formulation given in Table 2. The amount of each component is expressed in terms of weight percentage relative to a total weight (100%). The weight percentage of each component in the drug product suspension is on a wet basis (prior to removal of water). The weight percentage of each component in the rapidly infusing composition is on a dry basis (after removal of water).

TABLE 2

Example rapidly infusing composition formulation

| Ingredient | Drug product suspension % wt./wt. (wet) | Rapidly Infusing Composition wt./unit (dry) | Rapidly Infusing Composition % wt./wt. (dry) |
|---|---|---|---|
| Gelatin | 3.5 | 10.5 mg | 22.7 |
| Mannitol | 3.0 | 9 mg | 19.4 |
| Lemon-lime flavor powder | 0.2 | 0.6 mg | 1.3 |
| CBD isolate | 8.4 | 25 mg | 54.0 |
| Sucralose | 0.2 | 0.6 mg | 1.3 |
| Acesulfame-K | 0.2 | 0.6 mg | 1.3 |
| FD&C Yellow #5 | Trace | Trace | Trace |
| Purified water | 84.5 | Removed during manufacture | Removed during manufacture |
| Total | 100.0 | — | 100.0 |

Methods of Making the Rapidly Infusing Composition

Purified water was charged to a pot and mixed using an overhead stirrer as an agitating device.

With agitation, the requisite amount of gelatin and mannitol were dispersed, and the mixture was heated to 60° C. until the excipients were dissolved.

Once dissolved, the sweeteners sucralose and acesulfame-K were added and allowed to dissolve.

The solution was cooled to 30° C., moved to an overhead homogenizer, and then the requisite amount of cannabidiol (CBD) isolate was charged and dispersed using the homogenizer to micronize the CBD and create a drug product suspension.

The requisite amount of Lemon-Lime flavor was charged and mixed for 10 minutes, then the FD&C Yellow #5 colorant was added.

The resulting drug product suspension was transferred to a second overhead mixer and maintained at a temperature of 30° C. for the ensuing dosing operation.

In a blistering machine equipped with a dosing system, blister pockets were filled with a target dose weight of 300.0 mg of the drug product suspension.

The product was frozen in a suitable cryochamber and then the blister trays were transferred from the cryochamber to a suitable refrigerated storage cabinet (temperature below 0° C.) prior to lyophilizing to keep the product frozen.

The frozen blisters were loaded from the refrigerated storage cabinet into lyophilizers and the product was lyophilized (water was sublimated) to form the rapidly infusing compositions.

When the lyophilizing cycle was completed, the rapidly infusing compositions were transferred from the lyophilizers to the blistering machine where the blister trays were heat sealed with lidding material. The resulting tablets are flat-topped circular units approximately 15 mm in diameter with a convex bottom packaged in individual blister units (see also U.S. Provisional Application filed under attorney docket 532826US—incorporated herein by reference in its entirety).

The following tests were performed:
seal integrity test was performed at −0.5 Bar for 30 seconds, 1-minute soak time
Visual inspection was performed
Dry weight testing was performed Placebo A placebo product was also formulated in orally disintegrating tablet form in the same manner as the rapidly infusing composition, with the exception that the placebo product was formulated without CBD.

I. Method of Treating Postsurgical Pain Following Shoulder Arthroscopy

A double-blinded randomized controlled study will be performed to compare postoperative pain, patient satisfaction, and opioid use in two cohorts: patients undergoing shoulder arthroscopy who receive post-operative CBD in the form of the example rapidly infusing composition described above, and a placebo group. A total of 100 subjects will be enrolled (50 per cohort) meeting the following criteria:

Patients undergoing an arthroscopic shoulder procedure (rotator cuff repair, decompression, labrum repair)

Patients ages 18-75, inclusive

Female patients must be currently practicing effective forms of two types of birth control, which are defined as those, alone or in combination, that result in a low failure rate (less than 1% per year) when used consistently and correctly Male patients must be using an effective form of contraception.

Methods and Procedures

Patients indicated and scheduled for a shoulder arthroscopy will be identified from faculty surgeon case logs at the NYU Langone Health, Langone Orthopedic Hospital Sports Medicine Division. After informed consent is obtained, a chart review of patients' medications and past medical histories will be performed based on their electronic medical records to identify any current pain medications or exclusion criteria. In order to maintain the blind, the resident assisting the surgeon will randomize the patient to one of two cohorts using REDCap software. Both the resident and surgeon are members of the study team.

Cohort 1: rapidly infusing compositions (containing CBD) to be administered with routine post-operative pain management regimen Cohort 2: Will not receive CBD; but the visually indistinguishable placebo instead with routine post-operative pain management regimen.

The resident physician, physician assistant, anesthesiologist, surgeon and study team members will remain blinded. Additionally, all patients will receive a traditional upper extremity interscalene block as per routine.

All patients will receive a standardized regimen of PERCOCET (oxycodone/paracetamol) for pain management, which is standard of care post-operative treatment. Patients will receive a standard dose of 5/325 mg and be discharged with 30 tabs and will be instructed to take 1-2 tablets, as needed, every 4-6 hours.

Additionally, patients will be randomized into one of two cohorts. The first cohort will receive one tablet of the rapidly infusing composition (25 mg CBD), t.i.d., with instructions to take two tablets of the rapidly infusing composition if they weigh more than 80 kg (total maximum of 50 mg CBD per dose t.i.d.). Cohort 2 will receive the same instructions, but with the placebo instead.

All subjects will be required to refrain from use of THC, or other *cannabis*-related products for the duration of the study.

Information to be recorded pre-operatively includes age, sex, height, weight, BMI, American Society of Anesthesiology (ASA) classification, and suicidality assessment. As well as baseline levels of complete blood count (CBC), chemistry profile, liver enzymes, gamma glutamate transferase (GGT), electrocardiogram, urine analysis, 12-panel urine drug test, and a urine pregnancy test.

Intra-operative information will also be recorded, including operative time, procedure, number of anchors, and complications. Patients will subsequently be placed in different subgroups based on the procedure performed.

Pain severity scores at rest will be assessed by use of a visual analog scale (VAS; 0=no pain, 10=worst pain imaginable) at 6, 24, and 48 hours as well as 7 days and 14 days after surgery. Additionally, any nausea experienced by the patients will be recorded by use of a VAS (0=no nausea, 10=worst nausea imaginable) at 2 days, 7 days and 14 days after surgery. PERCOCET consumption will be recorded at 24 hours, 1 day, 2 days and 7 days, and 14 days after surgery. Additionally, CBD consumption will be recorded at 1 day, 2 days, 7 days and 14 days after surgery.

In addition to pre-operative liver function tests (LFTs), LFTs consisting of the standard hepatic panel, including serum transaminase and bilirubin levels, will be administered at the first post-operative visit, 10-14 days after the procedure.

Incidence of CBD-related side effects will be noted. Time to discharge from the postanesthesia care unit (PACU) and time to discharge from the hospital will be recorded. Patients will be in the study a duration of three months.

In order to maintain the blinding, all data, including pain severity scores, side effects, opioid and CBD consumption, will be collected by the resident physician or physician assistant.

It is believed that patients who have undergone shoulder arthroscopy receiving the rapidly infusing composition will: 1) experience less pain post-operatively compared to those patients who do not receive the rapidly infusing composition; 2) experience increased patient satisfaction compared to those patients who do not receive the rapidly infusing composition; 3) require less opioid use to manage pain compared to those patients who do not receive the rapidly infusing composition, and/or 4) experience fewer opioid-related side effects like nausea compared to those patients who do not receive the rapidly infusing composition.

II. Method of Treating Postsurgical Pain Following Knee Arthroplasty

A double-blind, randomized, controlled study will be performed to compare postoperative pain, patient satisfaction, nausea, and opioid use in two cohorts: patients undergoing knee arthroplasty who receive post-operative CBD in the form of the example rapidly infusing composition described above, and a placebo group. A total of 350 subjects (175 per cohort) will be enrolled meeting the following criteria:

Patients undergoing total knee arthroplasty and unicompartmental knee arthroplasty Patients ages 18-79, inclusive Female patients must be currently practicing effective forms of two types of birth control, which are defined as those, alone or in combination, that result in a low failure rate (less than 1% per year) when used consistently and correctly Male patients must be using an effective form of contraception.

Methods and Procedures

Patients indicated and scheduled for a knee arthroplasty will be identified from faculty surgeon case logs at the Princeton Orthopedic Associates. After informed consent is obtained, a chart review of patients' medications and past medical histories will be performed based on their electronic medical records to identify any current pain medications or exclusion criteria. In order to maintain the blind, the resident assisting the surgeon will randomize the patient to one of two cohorts using REDCap or other HIPAA-compliant software. Both the resident and surgeon are members of the study team.

Cohort 1: rapidly infusing compositions (containing CBD) to be administered with routine post-operative pain management regimen.

Cohort 2: Will not receive CBD; but the visually indistinguishable placebo instead with routine post-operative pain management regimen.

The resident physician, physician assistant, anesthesiologist, surgeon, and study team members will remain blinded.

Patients will receive a spinal block administered by the anesthesiologist immediately prior to surgery. An intraarticular block will be administered by the surgeon at the end of the procedure. Post-operatively in the postanesthesia care unit (PACU) an adductor canal peripheral nerve block will be administered by the anesthesiologist.

In-hospital, patients will receive TORADOL (ketorolac), 15 mg IV, q8 hours for the first 24 hours following surgery. Patients will not receive TORADOL at home. At home, patients will receive standard of care medication regimen consisting of either tramadol, oxycodone, or hydromorphone depending on their tolerance/intolerance; TYLENOL (acetaminophen); either LYRICA (pregabalin) or gabapentin for pain management; and either meloxicam or celecoxib for inflammation.

Patients will be discharged with 30 tablets of the prescribed opioid medication and instructed to follow standard dosing instructions depending on their level of pain and tolerance/intolerance of opioids, detailed in Table 3.

TABLE 3

| Medication | Dose | Dose Schedule | Maximum Dose mg/day |
|---|---|---|---|
| Tramadol (50 mg oral tablets) | 50-100 mg | Q4-6 PRN | 400 mg/day |
| OR if the patient does not tolerate Tramadol well, they will be prescribed either. | | | |
| Oxycodone (5 mg oral tablets) | 5-10 mg | Q4-6 PRN | As tolerated |
| OR | | | |
| Hydromorphone (2 mg oral tablets) | 2-4 mg | Q4-6 PRN | As tolerated |

Patients will also be instructed to take 1,000 mg of TYLENOL 3× per day, and LYRICA or gabapentin according to label instructions for approximately 14 days following surgery. Patients will take COLACE (docusate sodium) and pantoprazole as per post-operative joint replacement protocol.

Patients will be randomized into one of two cohorts. The first cohort will receive one tablet of the rapidly infusing composition (25 mg CBD), t.i.d., with instructions to take two tablets of the rapidly infusing composition if they weigh more than 80 kg (total maximum of 50 mg per dose t.i.d.). Cohort 2 will receive the same instructions, but with the placebo instead. Each cohort will be given a 10-day supply of either rapidly infusing composition or placebo.

All subjects will be required to refrain from use of THC, or other *cannabis*-related products for the duration of the study.

Information to be recorded pre-operatively includes age, sex, height, weight, BMI, American Society of Anesthesiology (ASA) classification, and suicidality assessment. In addition, baseline assessments for medical and physical history will be recorded, including: psychiatric exam, complete blood count (CBC), chemistry profile, liver enzymes, gamma-glutamate transferase (GGT), electrocardiogram, urine analysis, and urine pregnancy test.

Intra-operative information will also be recorded, including operative time, tourniquet time, procedure, and complications. Patients will subsequently be placed in different subgroups based on the procedure performed.

Time to discharge from the PACU and time to discharge from the hospital will be recorded.

Pain severity scores at rest will be assessed by use of a combination of the PROMIS sf v1.0 Pain Intensity 3a scale and the KOOS JR survey on Days 1-10 and at the first post-operative visit, typically 14 days after surgery.

Narcotic and CBD/placebo consumption will be recorded each day on Days 1-10, and at the first post-operative visit. There will also be a reconciliation of narcotic and rapidly infusing composition/placebo tablets at the first post-operative visit. Any unused rapidly infusing composition/placebo will be returned to the Investigator for disposal.

Any nausea experienced by the patients will be recorded by use of a visual analog scale (VAS; 0=no nausea, 10=worst nausea imaginable) on Days 1-10 and Day 14 after surgery.

In addition to the pre-operative liver function tests (LFTs), LFTs consisting of the standard hepatic panel, including serum transaminase and bilirubin levels, will be obtained 10-14 days after surgery either during the first post-operative office visit or via a homecare visit if required due to patient availability issues.

Incidence of CBD-related side effects will be recorded in patient journals.

In order to maintain the blinding, all data, including pain severity scores, side effects, opioid and CBD consumption, will be collected by the resident physician or physician assistant. Patients will be given an appointment to see their surgeon at 3 months following surgery (either in person or via telemedicine if necessary) but no data will be collected at this visit. Patients will be on treatment for up to 10 days, and in the study for a duration of up to three months.

It is believed that patients who have undergone knee arthroplasty receiving the rapidly infusing composition will: 1) experience less pain post-operatively compared to those patients who do not receive the rapidly infusing composition; 2) experience increased patient satisfaction compared to those patients who do not receive the rapidly infusing composition; 3) require less opioid use to manage pain compared to those patients who do not receive the rapidly infusing composition, and/or 4) experience fewer opioid-related side effects like nausea compared to those patients who do not receive the rapidly infusing composition.

III. Method of Treating Pancreatic Cancer-Associated Pain

A randomized, double-blind, placebo-controlled study will be performed to evaluate the efficacy and safety of CBD in the form of the example rapidly infusing composition described above versus placebo for the management of pain for patients with unresectable pancreatic cancer. The use of CBD, presented in the form of the rapidly infusing composition, will be evaluated as an adjunct to opioid and non-opioid analgesics for the reduction of cancer-associated pain, analgesic use, analgesic-related side effects, and the improvement in patient satisfaction/quality of life. 35 subjects during the first year of the study will be enrolled that meet the following criteria:

Locally advanced, unresectable (T4 or M1), or recurrent adenocarcinoma of the pancreas.
Presence of mid-abdominal pain (≥3 on VAS scale) at least 2 days per week, lasting at least 1 hour per day.
≥4 weeks since previous surgery.
Life expectancy≥3 months Registration A screening examination will be performed in the outpatient or inpatient setting to establish that all eligibility criteria are met. Screening assessment will include a VAS pain score. Eligible patients are to be scheduled for randomization and start of therapy vs placebo within 21 days following the screening visit. All baseline measures will be obtained after registration and immediately prior to the rapidly infusing composition initiation. Data requirements and scheduling are provided in Table 4.

TABLE 4

Schedule of assessments

| | | Months* | | |
|---|---|---|---|---|
| | Screen | Baseline | 1 | 3, 6, 12 |
| BPI | | X | X | X |
| FACT-P | | X | X | X |
| MSAS | | X | X | X |
| EQ-5D | | X | X | X |
| Pill count | | X | X | X |
| Weight/Height | | X | X | X |

MPAC: Memorial Pain Assessment Card; BPI: Brief Pain Inventory; MSAS: Memorial Symptom Assessment Scale; FACT-P: Functional Assessment of Cancer Therapy-Pancreas; Pill Count: Medication diary and direct pill count; Allowances for time intervals will be within 14 days for Months 1, 3, 6, 12.

Treatment Plan

Those participants that have provided written informed consent and have met all eligibility criteria will be randomized. Study participants will be randomized into one of two Cohorts, using a permuted block randomization method.

Cohort 1: Standard of Care pain management plus rapidly infusing compositions (containing CBD) to be administered as detailed below.

Cohort 2: Standard of Care pain management plus the placebo to be administered; will not receive CBD.

The study team members will remain blinded. Standard cancer and pain management will not be affected by this study.

Cohort 1 will be randomized to receive two tablets of the rapidly infusing composition (total of 50 mg per dose), t.i.d. Cohort 2 will receive the same instructions, but with the placebo instead.

All subjects will be required to refrain from use of THC, or other cannabis-related products for the duration of the study.

Information to be recorded includes age, sex, height, weight, BMI, American Society of Anesthesiology (ASA) classification, and suicidality assessment. As well as baseline levels of complete blood count (CBC), chemistry profile, liver enzymes (LFTs), urine analysis, 12-panel urine drug test, and a urine pregnancy test (if female).

Pain severity scores at rest will be assessed by use of a BPI which includes a visual analog scale (VAS; 0=no pain, 10=worst pain imaginable) at the time points noted above. Other opioid consumption will be recorded at the same time points. Additionally, CBD or placebo consumption will be recorded at the same time points after randomization. LFTs consisting of the standard hepatic panel, including serum transaminase and bilirubin levels, will be administered at the first post randomization visit at month 1.

Incidence of medication-related side effects will be noted using the Memorial Symptom Assessment Scale. In order to maintain the blinding, all data, including pain severity scores, side effects, opioid and CBD consumption, will be collected by the study nurse coordinator.

Standard of Care pain management: Medical treatment of pain will follow the "analgesic ladder" method of the World Health Organization (WHO) guidelines for cancer pain management for adults. Specific guidelines will be implemented for the purpose of the study and are as detailed in Tables 5 and 6.

TABLE 5

Algorithms for narcotic use in pain management

| | |
|---|---|
| No Pain | Consider Dose Reduction |
| Mild to Moderate Pain (VAS 1-3) | Increase dose 30% If maximal dose, add step 3 narcotic |
| Moderate to Severe Pain (VAS 4-7) | Increase dose 50% If maximal dose, add step 3 narcotic |
| Severe Pain (VAS >7) | Increase dose 100% If maximal dose, add step 3 narcotic Consider repeat celiac plexus block or alternative non-pharmacological method |

TABLE 6

Narcotic agents and dosing to be used

| Agent | Dose schedule | Starting Dose mg/d | Maximum Dose mg/d |
|---|---|---|---|
| Step 1 Agents | | | |
| Acetaminophen | Q4-6 | 2,600 mg/d | 6,000 mg/d |
| Ibuprofen | Q4-8 | 1,200 | 4,200 |
| Naproxen | Q12 | 500 | 1,000 |
| Indomethacin | Q8-12 | 75 | 200 |
| Ketorolac | Q6 | 10 | 60 |
| Step 2 Agents | | | |
| Aceto (300)-codeine (15) | Q4-6 | 2,400 mg/d (aceto) | 6,000 mg/d (aceto) |
| Aceto-oxycodone | Q4-6 | 2,600 mg/d (aceto) | 6,000 mg/d (aceto) |
| Aceto-propoxyphene | Q4-6 | 2,600 mg/d (aceto) | 6,000 mg/d (aceto) |
| Aceto-hydrocodone | Q4-6 | 2,600 mg/d (aceto) | 6,000 mg/d (aceto) |
| Step 3 Agents | | | |
| Morphine -SR (MS CONTIN) | Q8-12 | 60 mg/d | As tolerated |
| Morphine-IR (MSIR) | Prn-breakthrough | 60 mg/d | As tolerated |
| Hydromorphone | Q4-6 | 8 mg/d | As tolerated |
| Oxycodone-controlled release | Q12 | 20 mg/d | As tolerated |
| Fentanyl transdermal | Q48-72 hr | 25 microgr/hr | As tolerated |

In order to minimize confounding by radio-chemotherapy, enrollment will require that local radiotherapy to the epigastrium/pancreatic bed cannot be instituted or changed<7 days prior or <7 days after the start to rapidly infusing composition treatment.

Chemotherapy cannot be changed or a new regimen instituted<7 days prior or <7 days after the start of rapidly infusing composition treatment with the following exceptions: (i) chemotherapy may be discontinued at any time at the discretion of the treating physician; and (ii) patients who are receiving chemotherapy may have doses reduced for toxicity at the discretion of the treating physician.

All other clinically indicated care will be under the direction of the patients' oncologist, surgeons or gastroenterologists. Major interventions which could affect pain or quality of life including chemotherapy, radiotherapy, surgery, other pain control procedures (nerve block, acupuncture, herbal remedies, hypnosis) will be recorded at each scheduled study visits.

At the one-month visit the patient will be queried about any new symptoms, pain (VAS), fever (T>100), or weakness.

Patients will complete a Memorial Symptom Assessment Scale (32 items) which addresses narcotic specific side effects such as constipation, nausea, vomiting, somnolence, cognitive impairment, dysphoria, and myoclonus. Each side effect will be rated as mild, moderate, or severe.

Outcome Measures and Evaluation

The principal study outcomes (baseline and 1 month assessment) will be made by direct interview by the clinical study coordinator. Baseline measures will be collected at the registration visit prior to randomization. Office visits or virtual visits will be scheduled for 1 month (within 21-35 days), 2 months (6-10 weeks), 3 months (11-13 weeks), and 6 months (26 weeks) following the randomization. One, two, three and six month follow up measures will be obtained at those times. If a patient is unable to travel to the treating institution, the quality of life forms will be reviewed by telephone or video conference contact by the study coordinator. A brief physical examination including vital signs, weight, and abdominal exam will be obtained at each in-person visit. For patients' deaths occurring before the 3 month outcome, the highest VAS score from their pain/narcotic diary from the week before death will be used as the outcome measure.

The patient will complete a baseline estimation of the pain intensity, quality, distribution, and temporal relationship using the validated Brief Pain Inventory (BPI).

The patient will complete quality of life measures including the National Comprehensive Cancer Network Functional Assessment of Cancer Therapy (NCCN-FACT) Hepatobiliary-Pancreatic Symptom Index (NFHSI) (18 items) and the EQ-5D (5 items). The EQ-5D will also provide health state utilities (0-1 scale) for future economic studies. The Fact-P is a 9 item questionnaire which addresses disease specific symptoms including weight loss, bowel habits, appetite, and pain. The EQ-5D, formerly known as EuroQOL is a non-disease specific measure of quality of life and patient preferences. It is a 5 item questionnaire and VAS for overall health state. A major advantage of the EQ-5D is the ability to convert to a 0-1 scale of patient preferences which can be used to make quality adjusted life expectancy (QALE) estimations for clinical economic studies.

Performance status will be assessed using the Karnofsky scale to be assessed by the site investigator and/or their designee. The Karnofsky scale is a component of the Clinical Benefit Score, and thus is necessary for the outcome measures of this protocol.

Patients will be provided with a daily analgesic and pain scale diary. The diary will include daily pill consumption, and a single VAS scale for pain (the pain component of the MPAC). This diary, and direct pill/patch count will be verified at each office visit (month 1 and 3). All doses will be converted to morphine equivalents using standardized tables. The Clinical Benefit Score will be used to estimate the simultaneous effect of pain control and analgesic consumption. The CBS assesses the individual responses for pain, analgesic consumption, performance status and weight. To be considered a positive benefit, a patient must be positive for at least one primary element (pain, analgesic consumption, performance status or weight) without being negative for any of the others. This improvement must be persistent for ≥4 weeks. All weights will be obtained using the treating physicians' medical office scale. The Clinical Benefit Score will be measured as follows:

Primary Measures
  Pain
    Pain intensity (measured daily on the MPAC 0-100 VAS)
    Positive: An improvement of >50% from baseline for > weeks duration
    Negative: Any worsening from baseline sustained for 4 weeks.
    Stable: Any other result
  Analgesic Consumption (in morphine equivalents weekly)
    Positive: A decrease of >50% from baseline for >4 weeks
    Negative: Any worsening from baseline
    Stable: Any other result
  Karnofsky performance status
    Positive: An improvement of >20 points from baseline for >4 weeks
    Negative: Any worsening of >20 points from baseline for >4 weeks
    Stable: Any other results.
Secondary Measures
  Weight
    Positive: A gain of 7% from baseline sustained for 4 weeks
    Nonpositive: Any other result.

It is believed that patients experiencing pancreatic cancer-associated pain receiving the rapidly infusing composition will: 1) experience less pain compared to those patients who do not receive the rapidly infusing composition; 2) experience increased patient satisfaction/quality of life compared to those patients who do not receive the rapidly infusing composition; 3) require less narcotic use to manage pain compared to those patients who do not receive the rapidly infusing composition, and/or 4) experience fewer narcotic-related side effects like nausea compared to those patients who do not receive the rapidly infusing composition.

The invention claimed is:

1. A method of treating pain in a subject, comprising:
administering to the subject in need thereof, by placement in a buccal cavity, a lyophilized rapidly infusing composition comprising (a) a pharmaceutically acceptable binder and/or excipient system comprising bovine gelatin and a sugar alcohol, and (b) a therapeutically effective amount of cannabidiol (CBD) via buccal mucosa,
wherein the rapidly infusing composition is formulated with a solid form of the CBD having a purity between 95 and 99.9 wt. %, and wherein the rapidly infusing composition has a disintegration time of approximately 1 to 5 seconds in deionized water maintained at 37° C.±2° C.

2. The method of claim 1, wherein the bovine gelatin is present in the rapidly infusing composition in an amount of 10 to 35 wt. %, based on a total weight of the rapidly infusing composition on a dry basis.

3. The method of claim 1, wherein the sugar alcohol is present in the rapidly infusing composition in an amount of 5 to 35 wt. %, based on a total weight of the rapidly infusing composition on a dry basis.

4. The method of claim 1, wherein the CBD is present in the rapidly infusing composition in an amount of 20 to 70 wt. %, based on a total weight of the rapidly infusing composition on a dry basis.

5. The method of claim 1, wherein the solid form of the CBD has been micronized to have a D50 diameter between 1 and 50 μm.

6. The method of claim 1, wherein the rapidly infusing composition further comprises at least one selected from the group consisting of a sweetener, a flavorant, and a colorant.

7. The method of claim 1, wherein the therapeutically effective amount of CBD is from 10 to 100 mg of CBD per dose.

8. The method of claim 1, wherein the rapidly infusing composition is administered to the subject 1 to 10 times per day.

9. The method of claim 1, wherein the subject is a human.

10. The method of claim 1, wherein the pain is neuropathic pain.

11. The method of claim 1, wherein the pain is acute neuropathic pain.

12. The method of claim 1, wherein the pain is postsurgical pain and the rapidly infusing composition is administered post-operatively to the subject who has undergone a surgical procedure.

13. The method of claim 12, wherein the surgical procedure is knee arthroplasty.

14. The method of claim 12, wherein surgical procedure is shoulder arthroscopy.

15. The method of claim 1, wherein the subject has cancer and the pain is cancer-associated pain.

16. A rapidly infusing buccal composition, comprising:
bovine gelatin, in an amount of 10 to 35 wt. %, based on a total weight of the rapidly infusing buccal composition on a dry basis;
a sugar alcohol, in an amount of 5 to 35 wt. %, based on a total weight of the rapidly infusing buccal composition on a dry basis;
a therapeutically effective amount of cannabidiol (CBD), in an amount of 20 to 70 wt. %, based on a total weight of the rapidly infusing buccal composition on a dry basis;
wherein the rapidly infusing buccal composition is formulated with a solid form of the CBD having a purity between 95 and 99.9 wt. %, and wherein the rapidly infusing buccal composition is lyophilized and has a rapid disintegration time in a buccal cavity as demonstrated by a disintegration time of approximately 1 to 5 seconds in deionized water maintained at 37° C.±2° C.

17. The rapidly infusing buccal composition of claim 16, wherein the rapidly infusing buccal composition further comprises at least one selected from the group consisting of a sweetener, a flavorant, and a colorant.

18. The rapidly infusing buccal composition of claim 17, wherein the rapidly infusing buccal composition comprises the flavorant, and the flavorant comprises lemon-lime flavor.

19. The rapidly infusing buccal composition of claim 17, wherein the rapidly infusing buccal composition comprises the colorant, and the colorant comprises FD&C Yellow #5.

20. The rapidly infusing buccal composition of claim 16, wherein the solid form of the CBD has been micronized to have a D50 diameter between 1 and 50 μm.

21. The rapidly infusing buccal composition of claim 16, further comprising melatonin.

22. The rapidly infusing buccal composition of claim 16, wherein the CBD has a purity between 99 and 99.9 wt. %.

23. The rapidly infusing buccal composition of claim 16, wherein the bovine gelatin is present in an amount of 10 to 28 wt. %, based on a total weight of the rapidly infusing composition on a dry basis.

24. The rapidly infusing buccal composition of claim 16, wherein the bovine gelatin is present in an amount of 20 to 24 wt. %, based on a total weight of the rapidly infusing composition on a dry basis.

25. The method of claim 1, wherein the CBD has a purity between 99 and 99.9 wt. %.

26. A method of treating pain in a subject, comprising:
administering to the subject in need thereof via buccal mucosa, by placement in a buccal cavity, a lyophilized rapidly infusing composition comprising (a) a pharmaceutically acceptable binder and/or excipient system comprising 20 to 24 wt. % of bovine gelatin based on a total weight of the rapidly infusing composition on a dry basis, and a sugar alcohol, and (b) 20 to 55 mg of cannabidiol (CBD),
wherein the rapidly infusing composition is formulated with a solid form of the CBD having a purity between 99 and 99.9 wt. %, and wherein the rapidly infusing composition has a disintegration time of approximately 1 to 5 seconds in deionized water maintained at 37° C.±2° C.

27. The method of claim 1, wherein the subject is administered a total of from 75 to 150 mg of CBD per day in one or more doses comprising the rapidly infusing composition.

28. The method of claim 27, wherein the total of from 75 to 150 mg of CBD per day represents a dosage per weight of the subject of less than or equal to 1.875 mg/kg/day.

29. The method of claim 26, wherein the subject is administered a total daily dosage per weight of the subject that is less than or equal to 1.875 mg/kg/day.

30. The method of claim 1, wherein the rapidly infusing composition comprises less than 0.5 wt. % of surfactants and lubricants, based on a total weight of the rapidly infusing composition on a dry basis.

31. The rapidly infusing buccal composition of claim 16, wherein the rapidly infusing buccal composition comprises less than 0.5 wt. % of surfactants and lubricants, based on a total weight of the rapidly infusing composition on a dry basis.

32. The method of claim 26, wherein the rapidly infusing composition comprises less than 0.5 wt. % of surfactants and lubricants, based on a total weight of the rapidly infusing composition on a dry basis.

33. The method of claim 26, wherein the sugar alcohol is present in the rapidly infusing composition in an amount of 5 to 35 wt. %, based on a total weight of the rapidly infusing composition on a dry basis.

\* \* \* \* \*